US012702725B2

(12) United States Patent
Aly et al.

(10) Patent No.: US 12,702,725 B2
(45) Date of Patent: Aug. 11, 2026

(54) MOBILE DISINFECTION APPARATUSES HAVING VISUAL MARKER DETECTION SYSTEMS AND METHODS OF THEIR USE

(71) Applicant: Xenex Disinfection Services Inc., San Antonio, TX (US)

(72) Inventors: Sherif Aly, San Antonio, TX (US); Paul Froutan, Katy, TX (US); Mark Stibich, Santa Fe, NM (US); Nicholas Whitelonis, San Antonio, TX (US)

(73) Assignee: Xenex Disinfection Services Inc., San Antonio, TX (US)

( * ) Notice: Subject to any disclaimer, the term of this patent is extended or adjusted under 35 U.S.C. 154(b) by 803 days.

(21) Appl. No.: 18/096,999

(22) Filed: Jan. 13, 2023

(65) Prior Publication Data

US 2023/0149583 A1 May 18, 2023

Related U.S. Application Data

(63) Continuation of application No. PCT/US2020/042448, filed on Jul. 17, 2020.

(51) Int. Cl.
*A61L 2/24* (2006.01)
*A61L 2/07* (2006.01)
(Continued)

(52) U.S. Cl.
CPC .................. *A61L 2/24* (2013.01); *A61L 2/07* (2013.01); *A61L 2/084* (2013.01); *A61L 2/10* (2013.01);
(Continued)

(58) Field of Classification Search
CPC ... A61L 2/24; A61L 2/07; A61L 2/084; A61L 2/10; A61L 2/14; A61L 2/183;
(Continued)

(56) References Cited

U.S. PATENT DOCUMENTS 7,877,166 B2 1/2011 Harwig et al.
8,588,979 B2 11/2013 Decuir et al.
(Continued)

FOREIGN PATENT DOCUMENTS

GB 2551349 12/2017
JP H0291706 3/1990
(Continued)

OTHER PUBLICATIONS

International Searching Authority, International Search Report and Written Opinion for PCT Application No. US2020/042448 dated Apr. 23, 2021, 12 pages.

(Continued)

*Primary Examiner* — Lessanework Seifu
(74) *Attorney, Agent, or Firm* — Egan, Enders & Huston LLP.

(57) ABSTRACT

Mobile apparatuses and methods are provided that utilize visual marker detection (VMD) systems to determine and/or verify one or more locations in an area/room at which a mobile apparatus has been arranged and/or to determine and/or verify a mobile apparatus has been suitably positioned at a preset location in an area/room. Moreover, mobile apparatuses and methods are provided that utilize VMD systems to affect the operation of a mobile apparatus, particularly when and/or what manner the apparatus is operated. Furthermore, mobile apparatuses and methods are provided that utilize VMD systems to determine whether a mobile apparatus has moved to other locations in an area/room in a particular time frame, such as during operation of the apparatus. In addition, mobile apparatuses and methods are provided that utilize VMD systems to convey information that is specific to the location of the apparatus.

19 Claims, 6 Drawing Sheets

(51) Int. Cl.

| | |
|---|---|
| ***A61L 2/084*** | (2026.01) |
| ***A61L 2/10*** | (2006.01) |
| ***A61L 2/14*** | (2006.01) |
| ***A61L 2/183*** | (2026.01) |
| ***A61L 2/186*** | (2026.01) |
| ***A61L 2/208*** | (2026.01) |
| ***G16H 40/20*** | (2018.01) |

(52) U.S. Cl.
CPC ................. *A61L 2/14* (2013.01); *A61L 2/183* (2013.01); *A61L 2/186* (2013.01); *A61L 2/208* (2013.01); *G16H 40/20* (2018.01); *A61L 2202/14* (2013.01); *A61L 2202/16* (2013.01)

(58) Field of Classification Search
CPC . A61L 2/186; A61L 2/208; A61L 2/16; A61L 2202/14; A61L 2202/16; A61L 2202/25
See application file for complete search history.

(56) References Cited

U.S. PATENT DOCUMENTS

| | | | | |
|---|---|---|---|---|
| 9,697,393 | B2 | 7/2017 | Stagg et al. | |
| 9,794,741 | B2 | 10/2017 | Chaudri et al. | |
| 10,207,411 | B2 | 2/2019 | Michalakis | |
| 2005/0022330 | A1 | 2/2005 | Park et al. | |
| 2007/0202005 | A1 | 8/2007 | Maschke | |
| 2008/0147730 | A1 | 6/2008 | Lee et al. | |
| 2009/0198371 | A1 | 8/2009 | Emanuel et al. | |
| 2013/0087609 | A1 | 4/2013 | Nichol et al. | |
| 2016/0278868 | A1 | 9/2016 | Berend et al. | |
| 2017/0132581 | A1 | 5/2017 | Roman et al. | |
| 2017/0173195 | A1* | 6/2017 | Stibich ...................... | A61L 2/24 |
| 2017/0246331 | A1 | 8/2017 | Lloyd | |
| 2017/0312379 | A1 | 11/2017 | Stibich | |
| 2017/0330263 | A1 | 11/2017 | Shaffer | |
| 2018/0093380 | A1 | 4/2018 | Yoshida et al. | |
| 2018/0297207 | A1 | 10/2018 | Huang et al. | |
| 2019/0070324 | A1 | 3/2019 | Hardin et al. | |
| 2019/0117809 | A1 | 4/2019 | Katz | |
| 2020/0206375 | A1 | 7/2020 | Ufkes | |
| 2021/0046205 | A1* | 2/2021 | Copeland, Jr. ............ | A61L 2/24 |

FOREIGN PATENT DOCUMENTS

| | | |
|---|---|---|
| JP | 2018509993 | 4/2018 |
| JP | 2018122400 | 8/2018 |
| KR | 20060099832 | 9/2006 |
| WO | 2012033850 | 3/2012 |
| WO | 2015116876 | 8/2015 |
| WO | 2016089357 | 6/2016 |
| WO | 2017185138 | 11/2017 |
| WO | 2017191510 | 11/2017 |

OTHER PUBLICATIONS

European Patent Office, Office Action for European Patent Application No. 20751023.1 dated Mar. 15, 2024, 5 pages.

Japan Patent Office Patent, Notice of Reason for Refusal, Mailing Date Oct. 1, 2024, 3 pages.

* cited by examiner

Imaging Device 12
Integrated User Interface 20
26
10
Detached User Interface 22
Battery 24
Power Circuitry 14
Program Instructions 16
Processor 18

34
32
30
35
26
Imaging Device 12
Integrated User Interface 20
Detached User Interface 22
Motor 38
Power Circuitry 14
Remote Door Movement Sensor 39
Program Instructions 16
Processor 18
36
37

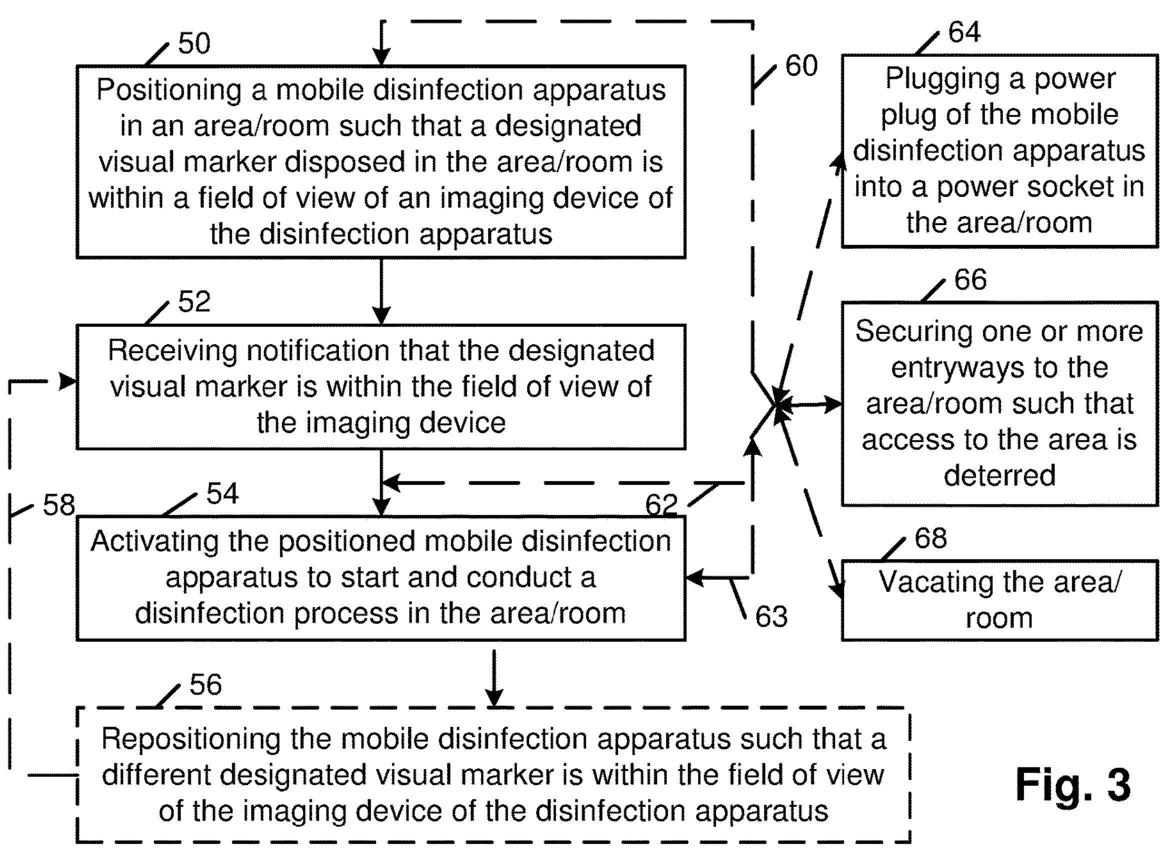
Fig. 3
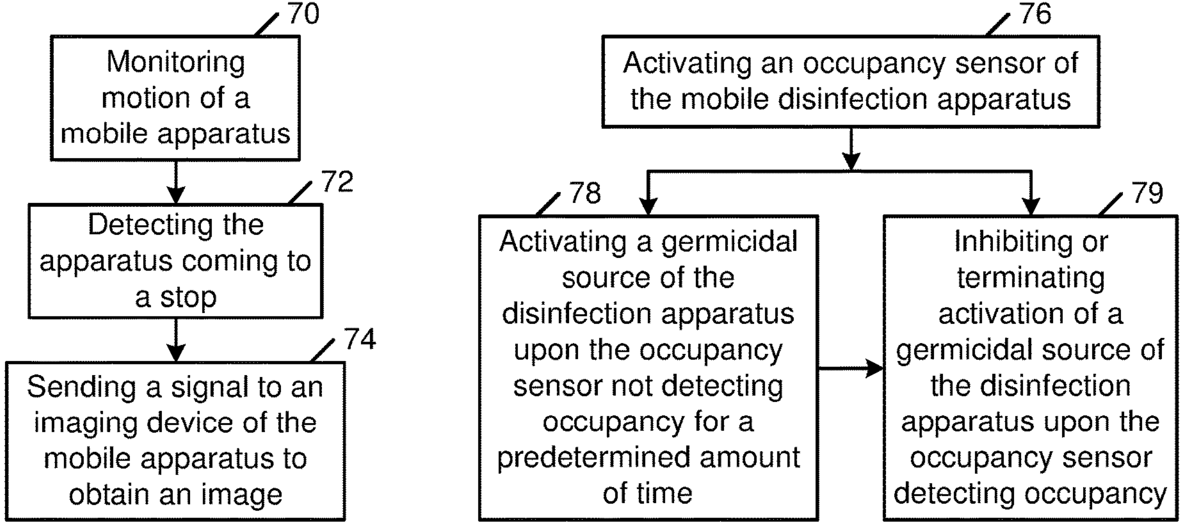
Fig. 4
Fig. 5

MOBILE DISINFECTION APPARATUSES HAVING VISUAL MARKER DETECTION SYSTEMS AND METHODS OF THEIR USE

PRIORITY CLAIM

This application is a continuation of pending International Patent Application No. PCT/US2020/042448 filed Jul. 17, 2020.

BACKGROUND OF THE INVENTION

1. Field of the Invention

This invention generally relates to mobile apparatuses having visual marker detection systems and, more particularly to, mobile disinfection apparatuses having visual marker detection systems and methods of their use.

2. Description of the Related Art

The following descriptions and examples are not admitted to be prior art by virtue of their inclusion within this section.

As pathogenic microorganisms have shown to be a leading cause of infections and contamination, area/room disinfection is becoming increasingly important, particularly in health-care environments, public areas having a large number and/or frequent turnover of people, and highly sensitive production applications (such as but not limited to those requiring cleanroom environments). Area/room disinfection systems come in a variety of configurations, depending on their design specifications. For example, some area/room disinfection systems are fixedly installed in a room/area, while others are portable. A challenge with many portable area/room disinfection systems is determining a location at which to position the system such that a disinfectant projected from the system is distributed in an efficient manner to a maximum number and/or to key surfaces in the area/room. In particular, the distribution of a disinfectant in many area/room disinfection systems is often limited by the distance an effective amount of the disinfectant may be projected. Underexposure of a disinfectant can leave a surface with an undesirably high number of pathogenic microorganisms, leaving it prone to continued contamination. Conversely, if an area/room disinfection device is placed in close proximity to a surface, the surface may be overexposed, which effectively is a waste of the disinfectant and potentially a waste of time and/or energy to perform a disinfection process. In view of this, it is sometimes desirable to position a portable area/room disinfection device at a predetermined location in an area/room, particularly a location which has been deemed to be adequate for an efficient distribution of a disinfectant from the disinfection device.

In addition or alternative to such an idea, it is sometimes desirable to know and/or verify one or more specific locations in an area/room in which a portable area/room disinfection device has been operated for a disinfection process, such as for compliance reporting or to be able to review the location/s in which a disinfection process was conducted. Conventional techniques for determining location/s of mobile device/s, however, have not proven to be reliable for determining specific location/s within an area/room. In particular, global positioning systems have been considered, but they are not generally reliable within buildings and do not provide sufficient resolution to provide a precise location in an area/room. In addition, radio frequency identification (RFID) systems have been suggested but have been proven to be too costly and/or not reliable enough to provide a precise location in an area/room. In particular, some RFID systems use ceiling or wall-based scanners which detect passive RFID tags on mobile object/devices within a certain proximity. RFID scanners, however, can be costly and, thus, in many facilities, RFID scanners may be only at the floor or unit level, not one in each room. Other attempts using RFID systems have included attaching an RFID scanner to a mobile object/device and locating the object/device by triangulating multiple RFID passive tags arranged at fixed locations in a room based on signal strength. This technique, however, has not proved to be reliable enough to provide a precise location in an area/room. In other applications, a user setting up a disinfection device may record an approximate location of the device for a subsequent disinfection process, but such a technique is prone to human error and would need to be independently verified to be relied upon for some compliance reporting.

Accordingly, it would be advantageous to develop methods for determining and/or verifying the location at which a portable disinfection device has been placed and/or operated in an area/room for a disinfection process. In addition, it would be beneficial to develop disinfection apparatuses which enhance such capability without being cost prohibitive or prone to human error. Moreover, it would be advantageous to develop mobile apparatuses having operations tied to the determination or verification of their specific location in an area/room.

SUMMARY OF THE INVENTION

Apparatuses having visual marker detection systems and methods of their use are provided. The following description of various embodiments of the apparatuses and methods is not to be construed in any way as limiting the subject matter of the appended claims.

An embodiment of a method for disinfecting an area includes positioning a mobile disinfection apparatus in an area/room such that a designated visual marker disposed in the area/room is within a field of view of an imaging device of the mobile disinfection apparatus. The method further includes receiving notification from a user interface in electrical communication with the mobile disinfection apparatus that the designated visual marker is within the field of view of the imaging device. Moreover, the method includes subsequently activating the positioned mobile disinfection apparatus to start and conduct a disinfection process in the area/room, wherein the mobile disinfection apparatus is configured to project a disinfectant into an ambient of the mobile disinfection apparatus during the disinfection process.

Embodiments of disinfection apparatuses include a germicidal source, an imaging device, and a controller having a processor and program instructions executable by the processor. In some cases, the program instructions are for decoding an image of a visual marker obtained by the imaging device to determine a position of the disinfection apparatus in a designated space and one or more operating parameters of the disinfection apparatus to conduct a disinfection process in the designated space. In such embodiments, the program instructions are further for activating the germicidal source and other components of the disinfection apparatus to conduct the disinfection process in accordance with the determined one or more operating parameters. In additional or alternative cases, the program instructions are for receiving an image of a visual marker obtained by the imaging device and subsequently activating the germicidal source and other components of the disinfection apparatus to start and conduct a disinfection process. In such embodiments, the program instructions are further for sending a signal to the imaging device to obtain one or more images during or after the disinfection process and determining whether the one or more other obtained images include the visual marker.

Another embodiment of a disinfection apparatus includes a germicidal source, an imaging device, a controller having a processor and program instructions executable by the processor for analyzing an image of a first visual marker obtained by the imaging device to determine whether the first visual marker is one of a set of designated visual markers associated with the disinfection apparatus. In addition, the program instructions are for releasing an operation lock on the apparatus subsequent to determining the first visual marker is one of the set of designated visual markers.

An embodiment of another apparatus includes an imaging device, wheels to affect mobility of the apparatus, a device for conveying information to a user of the apparatus, and a controller having a processor and program instructions executable by the processor. The program instructions are for receiving an image of a visual marker obtained by the imaging device, analyzing the image to determine a location of the apparatus within a structure, and sending one or more signals to the conveying device to convey location-specific information associated with the determined location.

BRIEF DESCRIPTION OF THE DRAWINGS

Other objects and advantages of the invention will become apparent upon reading the following detailed description and upon reference to the accompanying drawings in which:

FIG. 3 illustrates a flowchart of an example set of processes which may be performed by a user of a mobile apparatus or which may be incorporated into program instructions of a mobile apparatus; and FIGS. 4-12 illustrate flowcharts of examples of different sets of program instructions for the mobile apparatuses disclosed herein.

Figures 1, 2:
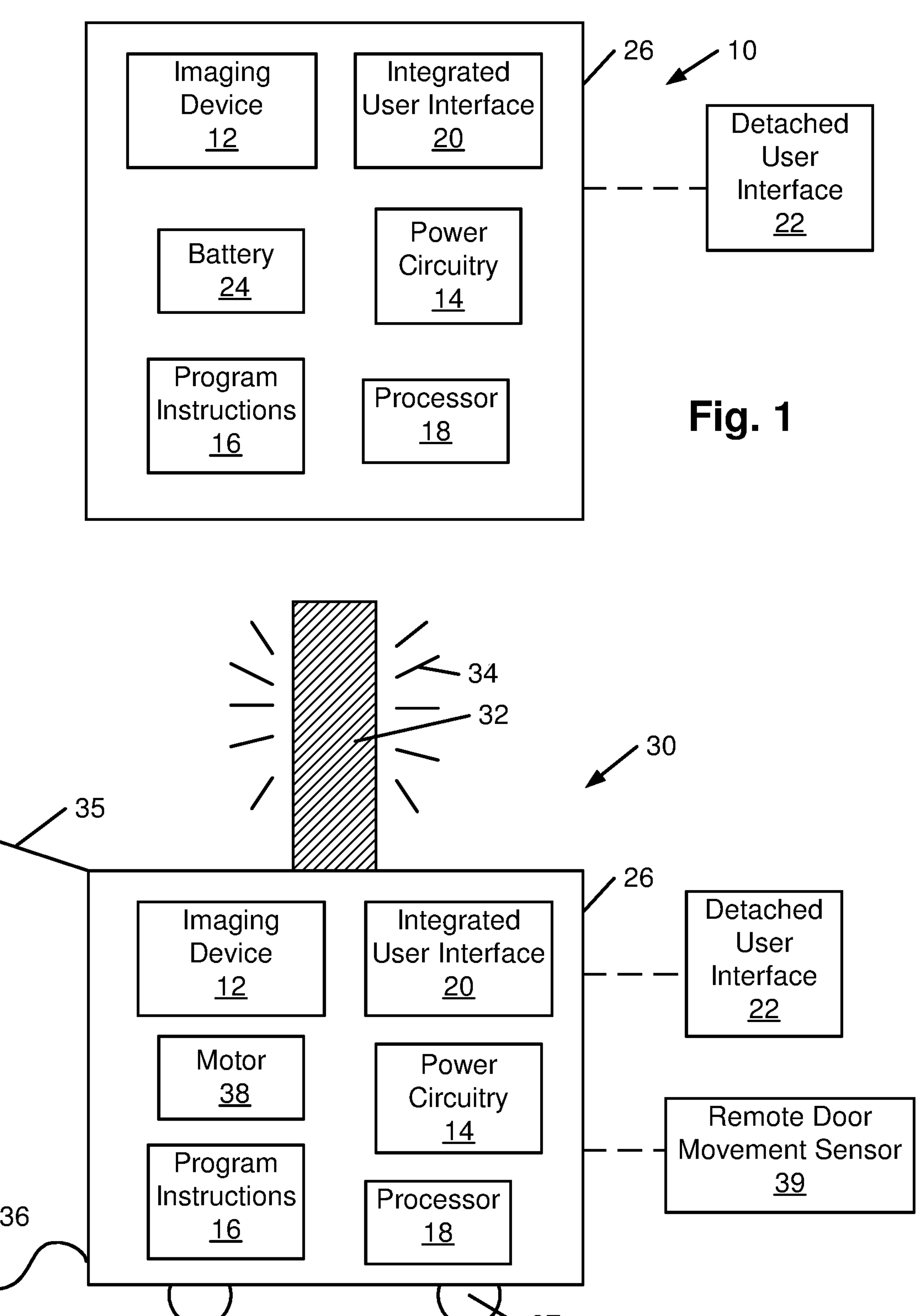
FIG. 1 illustrates an example of a mobile apparatus.
FIG. 2 illustrates an example of a mobile disinfection apparatus.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Mobile apparatuses and methods are provided that utilize visual marker detection systems to determine and/or verify one or more locations in an area/room at which a mobile apparatus has been arranged. In addition, mobile apparatuses and methods are provided that utilize visual marker detection systems to determine and/or verify a mobile apparatus has been suitably positioned at a preset location in an area/room or at a location in proximity or a preset distance from a device or object in an area/room. Moreover, mobile apparatuses and methods are provided that utilize visual marker detection systems to affect the operation of a mobile apparatus, particularly to control when and/or what manner the mobile apparatus is operated. Furthermore, mobile apparatuses and methods are provided that utilize visual marker detection systems to determine whether a mobile apparatus did or did not move to other locations in an area/room in a particular time frame, such as during operation of the apparatus. In addition, mobile apparatuses and methods are provided that utilize visual marker detection systems to convey information to a user of a mobile apparatus that is specific to the location of the mobile apparatus.

In general, the apparatuses considered herein are those that are configured to be mobile. As used herein, the terms "mobile" and "portable" refer to the capability of moving or being moved and may be used interchangeably herein. Configurations to affect mobility of the apparatuses considered herein may include but are not limited to wheels (motorized or non-motorized), one or more handles, navigational program instructions (including preprogrammed paths, navigation via remote control and/or autonomous capability), a weight and design which affords the apparatus to be efficiently and safely transported at least 1 meter, or any combination thereof. It is emphasized that the apparatuses considered herein may include any one or more of such configurations in any combination to affect its mobility and, thus, the apparatuses are not limited to including all of the noted configurations. For instance, an apparatus having motorized wheels may or may not include navigational program instructions. Furthermore, an apparatus configured for autonomous movement may or may not include a handle. Moreover, an apparatus having one or more handles may or may not have wheels and vice versa. In addition, an apparatus with wheels is generally easier to push or pull than an apparatus without wheels and, thus, apparatuses considered herein having wheels may be but are not necessarily heavier than those without wheels. In any case, all references of an apparatus having wheels disclosed herein refers to an apparatus having a device of a wheel attached to an axle. In some cases, the wheels of an apparatus considered herein may be casters.

In general, the parameters constituting "a weight and design which affords the apparatus to be efficiently and safely transported at least 1 meter" may vary among apparatuses. For instance, in cases in which an apparatus is not motorized, the phrase may pertain to an ergonomic weight and design which affords the apparatus to be efficiently and safely carried, pushed and/or pulled at least 1 meter by one or more adults of average height and weight. For example, the weight of an apparatus considered herein that is not motorized may, in some cases, be less than approximately 25 pounds, particularly but not limited to if the apparatus does not include wheels and is of a design (i.e., size, shape, etc.) that one individual may manipulate the relocation of the apparatus. Alternatively, the weight of an apparatus considered herein that is not motorized may, in some cases, be more than approximately 25 pounds but less than approximately 200 pounds, particularly if the apparatus includes wheels and/or is of a design that facilitates multiple individuals to manipulate the relocation of the apparatus (e.g., includes multiple handles). In yet other embodiments, the weight of an apparatus considered herein that is not motorized and has wheels and/or has a design that multiple individuals may manipulate the relocation of may be less than approximately 25 pounds.

In alternative embodiments, the apparatuses considered herein may be motorized and, in such cases, the weight of an apparatus may not be as restricted as those which are not motorized, particularly an apparatus which is motorized may be any weight and design which affords the apparatus to efficiently and safely travel at least 1 meter. For example, an apparatus considered herein that is motorized may include a weight and motor controls which allow the movement of the apparatus to be started and stopped without undue time delay (e.g., less than 5 seconds from the receipt of signals to start and stop movement of the apparatus). In addition, an apparatus considered herein that is motorized may include a weight, speed controls, and/or navigational controls which allows the apparatus to be moved without causing damage to the apparatus or infrastructure along the path of the apparatus. For instance, an apparatus considered herein that is motorized may include navigational controls which prevent the apparatus from bombarding with obstacles and/or walls. In addition or alternatively, an apparatus considered herein that is motorized may be configured to limit the speed of the apparatus, but yet enable speeds such that an apparatus may travel to a position in a timely manner, particularly regarding the idea of the apparatuses considered herein being configured to efficiently travel at least 1 meter. An example range of speed for the apparatuses considered herein may be up to approximately 200 meter/minute, but faster speeds may be considered.

In any case, an apparatus that is motorized may include configurations for a user to guide the apparatus and/or configurations for the apparatus to autonomously guide itself. Example configurations which may enable a user to guide a mobile apparatus include one or handles and/or one or more user input controls, such as but not limited to a steering wheel, a joystick, a means for enabling audible input for directional movement and/or one or more tactile input controls denoting particular directional movements (such as but not limited to buttons, switches, graphical user interfaces and/or touch sensor means). In some cases, configurations for enabling a user to guide an apparatus may be integrated into the apparatus such that movement of the apparatus may be controlled at the apparatus. In some of such scenarios, an apparatus may include configurations to accommodate a user guiding the apparatus, such as a seat if the mobile apparatus is a vehicle (e.g., a user driven floor cleaner) and/or shields if movement of the mobile apparatus is susceptible to exposing the user to harm. In yet other cases, user input controls for enabling a user to guide an apparatus may be integrated into a detached user interface used in conjunction with the apparatus such that movement of the apparatus may be controlled via remote control. In some cases, a mobile apparatus may include configurations integrated into the apparatus and configurations integrated into a detached user interface for enabling a user to guide its movement. In yet other cases, a mobile apparatus may be additionally or alternatively configured to guide itself, i.e., via program instructions to follow a predetermined path and/or via navigational controls for autonomous movement.

Further to the idea of the mobile apparatuses described herein being configured to be efficiently transported at least 1 meter, the apparatuses considered herein (regardless of whether they are motorized or not) may, in some cases, be specific to those which do not require a significant amount of time (e.g., not more than 5 seconds) to start movement of the apparatus across an area or room. As such, the apparatuses considered herein do not embody apparatuses which are screwed or bolted to a surface for its operation. Moreover, the mobile apparatuses disclosed herein may include guarding which allows the apparatus to be moved without causing damage to the apparatus or infrastructure along the path of the apparatus. For example, the mobile apparatuses disclosed herein may have bumpers along an outermost periphery of the apparatus. In addition or alternatively, the mobile apparatuses disclosed herein may have their fragile components arranged in protective housings and/or arranged inward from an outermost periphery of the apparatus.

The term "area/room", as used herein, refers to a space in a building which is suitable for human occupancy. The phrase "a space which is suitable for human occupancy", as used herein, refers to a space in which an adult human being of average size may comfortably occupy for at least a period of time to eat, sleep, work, lounge, partake in an activity, or complete a task therein. In some cases, spaces suitable for human occupancy may be a room, which is referred to herein as a space bounded by walls, ceiling, flooring, and one or more doors for entering and exiting the space. In other cases, a space suitable for human occupancy may be an area with less than all of the boundaries which characterize a room. Examples of spaces which are suitable for human occupancy include but are not limited to single patient rooms, multiple occupancy patient rooms, bathrooms, walk-in closets, hallways, bedrooms, offices, operating rooms, patient examination rooms, waiting and/or lounging areas, nursing stations, laboratories, clean rooms, stock/equipment rooms, work stations, cubicles, hotel rooms, meeting/party rooms, gyms, work-out rooms, locker rooms, classrooms, store merchandising floors, store aisles, library aisles and sitting areas, airplane cabins, cockpits, watercraft cabins and vehicles.

Examples of buildings which may be particularly applicable for the use of the methods and apparatuses disclosed herein include but are not limited to healthcare facilities (including but not limited to hospitals, urgent care facilities, clinics, nursing homes, outpatient surgical facilities, birth centers, dialysis centers, hospice centers and blood banks), pharmaceutical laboratories and plants, childcare facilities, fitness centers, food manufacturing and/or processing facilities, animal care centers, agricultural buildings, office buildings, stores, hotels, schools and libraries. The apparatuses and methods disclosed herein may also be used in various types of aircraft and watercraft, including but not limited to airplanes, jets, helicopters, cruise ships, boats, and submarines.

In general, areas/rooms which may be considered for the methods disclosed herein as well as for use of the mobile apparatuses and systems disclosed herein may have a footprint greater than approximately 25 $ft^2$, but smaller areas/rooms may be considered. In some cases, areas/rooms which may be considered particularly suited for the methods disclosed herein as well as for use of the mobile apparatuses disclosed herein may have a footprint greater than approximately 100 $ft^2$. In particular, it is contemplated that it may be particularly beneficial to determine and/or set an approximate position of a mobile apparatus in a relatively large area/room due to the increased variability of where the apparatus may be positioned therein. For example, as set forth in more detail below, a mobile apparatus considered for the methods and apparatuses disclosed herein may be an apparatus in which the efficacy of its operation is affected by its location in an area/room and, in some cases, may be affected by the distance the apparatus is to surfaces in the area/room. The variability of the efficacy of such a mobile apparatus is proportional to the size of area/room in which it is used and, thus, the methods and apparatuses disclosed herein may be particularly suited for relatively large areas/rooms in an effort to control the efficacy of the mobile apparatus.

In some embodiments, a mobile apparatus considered herein may have a maximum height of approximately 75 inches and/or a maximum width of approximately 70 inches, and in particular cases, a maximum width of approximately 32 inches. In particular, such size restrictions may be advantageous in embodiments in which a mobile apparatus is to be used in different spaces in a structure some of which have limited access for entry, such as through a door or a passageway having the width of a door. More specifically, in order to accommodate the use of a mobile apparatus in such spaces, the mobile apparatuses disclosed herein may have size limitations such that they may be moved into the spaces through their entryways. In cases in which a mobile apparatus considered herein is to be used in narrower spaces, such as but not limited to an airplane aisle, the maximum width of the apparatus may be narrower, such as less than approximately 15 inches. In other cases, a mobile apparatus considered herein may be used in spaces which are not limited by the size of the space in which they are to be used or the size of its entry and, thus, the mobile apparatuses used in such spaces may not have the aforementioned width and/or height limitations.

Regardless of its size, a mobile apparatus considered herein may, in some cases, be an apparatus that is configured to conduct an operation which affects or is affected by the ambient of the apparatus. For instance, mobile floor cleaners (including those which are self-driven and those which are user-driven) may be considered for the features and methods disclosed herein. Furthermore, a mobile apparatus considered herein may be one which the efficacy of its operation is affected by its location in an area/room. Examples of mobile apparatuses which are configured to conduct such operations may include but are not limited to mobile area/room disinfection apparatuses, mobile air purifiers, mobile motion detectors, mobile heating and/or cooling devices, mobile air quality analyzers and mobile light fixture pathogen detectors. In particular, each of such apparatuses conduct operations which involve the ambient in which they are arranged and, furthermore, their efficacy may be affected by the specific location in the area or room which the apparatus is arranged, depending on the size and configuration of the room.

For instance, for mobile area/room disinfection apparatuses which are configured to project and/or distribute a germicidal agent into an ambient of an area/room in which it is arranged, its disinfection efficacy on intended surfaces of the area/room depends at least in part on the distance to those surfaces. As such, the efficiency to disinfect surfaces within the entire area/room may depend on the position of the mobile area/room disinfection apparatus in the area/room while it conducts a disinfection process. Moreover, for mobile motion detectors which are configured to detect movement in an ambient of an area/room in which it is arranged, its efficacy to detect motion in one or more particular regions of the area/room may depend on the position of the motion detector in the area/room (depending on the sensor technology used for the motion detector) and, in some cases, specifically whether the motion detector is placed in a line of sight of the particular regions. Furthermore, mobile air purifiers and mobile air quality analyzers are configured to drawn in air from an ambient of the apparatus and discharge the air into an ambient of the apparatus and their efficacy to heat, cool, circulate, disinfect and/or analyze the air in a portion or an entirety of an area/room is affected by its position in the area/room.

As set forth in more detail below, the apparatuses and methods disclosed herein are emphasized in reference to mobile disinfection apparatuses and, more specifically, in reference to mobile area/room disinfection apparatuses and methods for disinfecting surfaces in an area/room. The scope of the ideas set forth herein, however, need not be so restricted. In particular, the methods and apparatuses disclosed herein may be applied to any mobile apparatus and may be particularly applicable to those which are configured conduct an operation which affects or is affected by the ambient of the apparatus and the efficacy of its operation is affected by its location in an area/room in which it is arranged as set forth above. As such, although the methods and apparatuses described in reference to FIGS. 3-12 below are specific to mobile disinfection apparatuses and methods for disinfecting an area/room, the features of the apparatuses are not necessarily limited to disinfection apparatuses and the processes outlined in the methods are not necessarily limited to disinfecting an area/room. On the contrary, it is contemplated that the processes and apparatus features disclosed in reference to FIGS. 3-12 may be applied to any mobile apparatus constituted by any one or more of the provisions described above for characterizing an apparatus to be mobile. It is particularly contemplated that any of the processes and apparatus features disclosed in reference to FIGS. 3-12 may be applied to mobile floor cleaners, mobile air purifiers, mobile motion detectors, mobile heating and/or cooling devices, mobile air quality analyzers and mobile light fixture pathogen detectors.

In addition to being configured for mobility, each of the mobile apparatuses considered herein includes an imaging device, a processor and program instructions for affecting operations of the mobile apparatus in relation to an image received from the imaging device. The imaging device includes an image sensor and an electronic imaging device. The image sensor may be any sensor configured to detect and convey information to make an image, such as but not limited a complementary metal-oxide-semiconductor (CMOS) sensor or a charge-coupled device (CCD). The electronic imaging device be any device configured to process information (i.e., signals) received from the image sensor to create an image, such as but not limited to a camera (including still image cameras and video cameras) or a scanner. The program instructions are executable by the processor for detecting and, in some cases, analyzing an image received from the imaging device and, if applicable, affecting operations of the apparatus in relation to the image. Examples of program instructions for affecting operations of the apparatus based on the image received from the imaging device are described in more detail in reference to FIGS. 3-12.

Analyzing an image received from the imaging device may take different forms, including but not limited to comparing the image to a database of images, comparing the image to one or more previous images taken by the imaging device, analyzing the size, shape, contour, clarity and/or placement of a visually identifiable mark in the image, and/or decoding the image. In addition, the objective of the image analysis may vary, particularly whether it is used to verify a mobile disinfection apparatus has been properly positioned at a location in an area/room, to determine whether a visual marker in the image is associated with the mobile disinfection apparatus, to determine whether the mobile disinfection apparatus has moved from a location of a previous disinfection process, to determine whether the disinfection apparatus has moved during a disinfection process, to determine operational parameters of the mobile disinfection apparatus, and/or to determine location information associated with the area/room in which the visual marker is disposed. Examples of different analysis processes are described in more detail below in reference to FIGS. 6-12.

Turning to the drawings, schematic drawings of example mobile apparatuses are shown in FIGS. 1 and 2. In particular, FIGS. 1 and 2 respectively illustrate mobile apparatus 10 and mobile disinfection apparatus 30 each having imaging device 12, power circuitry 14, program instructions 16, processor 18 and integrated user interface 20. In addition, each of apparatuses 10 and 30 are communicably coupled to detached user interface 22. Apparatuses 10 and 30 differ in that mobile disinfection apparatus 30 includes germicidal source 32 arranged such that germicide 34 is projected into an ambient of apparatus 30. In addition, mobile disinfection apparatus 30 includes power plug 36 while mobile apparatus 10 includes battery 24. Moreover, mobile disinfection apparatus 30 includes handle 35, wheels 37 to affect its mobility and optionally motor 38 to automate movement of wheels 37. Furthermore, mobile disinfection apparatus 30 is communicably coupled to remote door movement sensor 39. It is noted, however, the inclusion and/or configuration of germicidal source 32, power plug 36, handle 35, wheels 37, motor 38 and door movement sensor 39 are not mutually exclusive to mobile disinfection apparatus 30, nor is battery 24 mutually exclusive to mobile apparatus 10.

On the contrary, mobile apparatus 10 may, in some embodiments, include a germicidal source. Furthermore, mobile disinfection apparatus 30 may include a battery in addition to or alternative to power plug 36 and, conversely, mobile apparatus 10 may include a power plug in addition or alternative battery 24. Moreover, mobile disinfection apparatus 30 may, in some cases, be void of motor 38 and, in particular embodiments, may be void of wheels 37 and/or handle 35. In addition, mobile apparatus 10 may, in some cases, include wheels to affect its mobility and optionally a motor to automate movement of the wheels. Furthermore, mobile apparatus 10 may include a door movement sensor and/or mobile disinfection apparatus 30 may not include door movement sensor 39. In any case, mobile apparatuses 10 and 30 are those which are portable. Thus, in addition or alternative to having wheels and optionally a motor to automate movement of the wheels, mobile apparatuses 10 and 30 may include other configurations to affect mobility of the apparatuses such as one or more handles, navigational program instructions (including preprogrammed paths, navigation via remote control and/or autonomous capability), a weight and design which affords the apparatus to be efficiently and safely transported at least 1 meter, or any combination thereof.

As noted above and shown in FIGS. 1 and 2, features common to both mobile apparatuses 10 and 30 include imaging device 12, power circuitry 14, program instructions 16, processor 18, integrated user interface 20 and detached user interface 22. In general, power circuitry 14, program instructions 16 and processor 18 is in electrical communication (via wired or wireless connections) with each other and other components of the apparatuses (such as but not limited to imaging device 12, integrated user interface 20, detached user interface 22, battery 24, power plug 36, germicidal source 32, motor 38 and/or remote door movement sensor 39) to affect operations of the apparatus. For instance, power circuitry 14 is electrically coupled to germicidal source 32 of mobile disinfection apparatus 30 of FIG. 2 to operate the germicidal source, particularly to activate the germicidal source to project and, in some cases, generate a germicide. In addition, power circuitry 14 is electrically coupled to processor 18 and possibly integrated user interface 20, detached user interface 22 and/or other components of mobile disinfection apparatus 30 to affect the timing at which to operate germicidal source 32. Other electrical connections may be included in mobile apparatuses 10 and 30 between any of the components of mobile apparatuses 10 and 30 to affect operations thereof. For example, power circuitry 14, processor 18, integrated user interface 20 and/or detached user interface 22 may be in electrical communication with an air moving device, sensors, actuators, other germicidal sources or any other components optionally included in the apparatuses to affect their operation. In any case, FIGS. 1 and 2 illustrate imaging device 12, power circuitry 14, program instructions 16, processor 18, integrated user interface 20, battery 24 and motor 38 all internal to casing 26 of the apparatuses. In other cases, one or more of such components may be arranged in a distinct casing. In either case, the shape of the casing may differ from the rectangular shape shown in FIGS. 1 and 2.

In general, processor 18 is electrically coupled to program instructions 16 such that the program instructions may be executed by the processor and, in addition, processor 18 is electrically coupled to integrated user interface 20, detached user interface 22, imaging device 12 and/or sensors of apparatus to affect operations other components of the apparatus in accordance with program instructions 16. For example, processor 18 is electrically coupled to imaging device 12 to affect program instructions 16 for receiving and/or analyzing images received from the imaging device and for affecting further operations of the apparatus based on the received and/or analyzed images. Examples of program instructions for affecting operations of an apparatus based on an image received from an imaging device are described in more detail in reference to FIGS. 3-12.

The term "program instructions", as used herein, refers to commands within software which are configured to perform a particular function, such as but not limited to any combination of the processes described in reference to FIGS. 3-12. It is noted program instructions 16 may include program instructions for performing processes other than those specifically described herein and, thus, the apparatuses described herein are not limited to having program instructions for performing the operations described in reference to FIGS. 3-12. Program instructions 16 may be implemented in any of various ways, including procedure-based techniques, component-based techniques, and/or object-oriented techniques, among others. In addition, program instructions 16 may be transmitted over or on a carrier medium such as a wire, cable, or wireless transmission link. In general, program instructions 16 may be stored in a storage medium within the apparatuses described herein. The term "storage medium", as used herein, refers to any electronic medium configured to hold one or more set of program instructions, such as but not limited to a read-only memory, a read-write memory, a random-access memory, a magnetic or optical disk, or magnetic tape.

As mentioned above and shown in FIGS. 1 and 2, mobile apparatuses 10 and 30 may include integrated user interface 20 and may also be communicably coupled to detached user interface 22. However, neither apparatus needs to include both user interfaces. As such, in some embodiments, either or both of mobile apparatuses 10 and 30 may be void of integrated user interface 20 or, alternatively, either or both of mobile apparatuses 10 and 30 may not be communicably coupled to detached user interface 22. Alternatively stated, each of mobile apparatuses 10 and 30 may at least be associated with one of integrated user interface 20 and detached user interface 22 and, in some cases, both interfaces, but in other cases, just one of such interfaces.

Integrated user interface 20 differs from detached user interface 22 in that it is fixedly integrated into the mobile apparatus and functions by the power supplied to the mobile apparatus, such from a battery and/or a mains supply power cord of the mobile apparatus. On the contrary, detached user interface 22 is integrated into a device or system that is distinct from mobile apparatuses 10 and 30 and functions by a power source that is distinct from mobile apparatuses 10 and 30. The power source accessed by detached user interface 22 may be a battery in the device or system in which the detached user interface is incorporated and/or may be mains power supplied via a power connection (e.g., a power cord or circuitry) of the device or system in which the detached user interface is incorporated. In any case, the device or system in which detached user interface 22 is incorporated is configured for wireless communication with the mobile apparatus it is associated with (e.g., mobile apparatuses 10 and/or 30). More specifically, the device or system in which detached user interface 22 is incorporated (as well as mobile apparatuses 10 and/or 30) include wireless receivers and/or transmitters to facilitate the transfer of communication signals between the devices.

In some cases, a device or system comprising detached user interface 22 may be mobile and, more specifically, may be independently mobile from mobile apparatuses 10 or 30. Reference is made to the definition of the term "mobile" provided herein for configurations which may constitute a device or system comprising detached user interface 22 to be mobile and is not reiterated for the sake of brevity. Examples of mobile devices or systems on which detached user interface 22 may be installed include but are not limited to handheld devices (such as but not limited to cell phones and electronic tablets) as well as desk top computers and an accompanying computer monitor. In some cases, a mobile device or system comprising detached user interface 22 and/or mobile apparatuses 10 and/or 30 may be configured such that the mobile device or system may be easily attached and detached from mobile apparatuses 10 and/or 30. In some of such cases, detached user interface 22 and mobile apparatuses 10 and/or 30 may be configured for the detached user interface 22 to access power supplied to the apparatus to use as an alternative to its own power source and/or to a charge a battery of the device comprising detached user interface 22. In alternative cases, a device or system comprising detached user interface 22 may not be mobile. Examples of non-mobile devices or systems in which detached user interface 22 may be installed include but are not limited to those mounted on a surface by screw/s and/or bolt/s.

In some cases, integrated user interface 20 and/or detached user interface 22 may include input controls to affect operation of mobile apparatuses 10 and 30, such as but not limited to a start and stop button to enable a user to start and terminate an operation of mobile apparatuses 10 and 30 and/or input controls allowing selection of different operation modes conducted by the apparatuses. Configurations of input controls for integrated user interface 20 and detached user interface 22 may include any of those known in the art, including but not limited to buttons, switches, graphical user interfaces, touch sensor means and means for enabling audible input. In some cases, the input control/s of detached user interface 22 may be specific to controlling operation of a single particular mobile apparatus, but in other cases detached user interface 22 may include input control/s to control operations of a plurality of mobile apparatuses. In yet other cases, the device or system comprising detached user interface 22 may be a device or system having multiple computer applications (commonly referred to as "apps") for accessing or controlling a multitude of items, some of which may have nothing to do with mobile apparatuses 10 or 30. An example of a device having such a configuration is a smartphone, but other electronic devices may be considered for the detached user interface 22.

In some cases, mobile apparatus 10 and/or 30 be configured to receive signals and output information pertaining to such signals to one or more information conveying devices to inform a user of the apparatus. In some cases, the one or more information conveying devices may be part of user interface 20 and/or detached user interface 22. In other cases, mobile apparatus 10 and/or 30 may include one or more information conveying devices separate from integrated user interface 20 and/or detached user interface 22 (i.e., the information conveying devices are not included in the same module as integrated user interface 20 and/or detached user interface 22). In any case, configurations of the information conveying device/s may include any visual indicator, visual display or audible means known in the art.

Examples of information output to an information conveying device may include but are not limited to the position of the mobile apparatus relative to a visual marker detected by imaging device 12, notice that a visual marker is within the field of view of an imaging device of the mobile apparatus, notice of whether or not the mobile apparatus is in a suitable position for operation of the apparatus, notice of whether an operation lock on the mobile apparatus is activated or has been released, status of tasks to be completed prior to, during, or subsequent to an operation of the mobile apparatus, the amount of time expired and/or remaining for a given operation of the mobile apparatus, notice that the mobile apparatus is in operation or not in operation, notice of the operation mode to be, being or previously conducted by the mobile apparatus, operational parameters and/or results of an operation of the mobile apparatus, notice of an operational error by the mobile apparatus, and/or notice of an early termination of an operation conducted by the mobile apparatus.

As mentioned above and shown in FIGS. 1 and 2, mobile apparatuses 10 and 30 include imaging device 12. In general, imaging device 12 includes an image sensor and an electronic imaging device. The image sensor may be any sensor configured to detect and convey information to make an image, such as but not limited a complementary metal-oxide-semiconductor (CMOS) sensor or a charge-coupled device (CCD). The electronic imaging device be any device configured to process information (i.e., signals) received from the image sensor to create an image, such as but not limited to a camera (including still image cameras and video cameras) or a scanner. As set forth in more detail below, imaging device 12 may be used to position mobile apparatus 10 and/or 30 relative to a visual marker, may be used to detect a visual marker, and/or may be used to create images by which the mobile apparatus may include program instructions to analyze for affecting operations of the apparatus and/or conveying information based on the analyzed images. The combination of imaging device 12 with any of the configurations described below to enable such uses of imaging device 12 may generally constitute a visual marker detection system of apparatuses 10 and 30.

For instance, in cases in which imaging device 12 is used to position mobile apparatus 10 or 30 relative to a visual marker, the mobile apparatus may be equipped with a visual display (i.e., on its main unit and/or on detached user interface 22) for displaying what imaging device 12 is currently viewing. In such cases, the visual display may be a video display of the view or may be a computer-generated representation of the view. In either case, the visual display and imaging device 12 may be used in conjunction to aid in positioning mobile apparatus 10 or 30 relative to a visual marker, particularly a user of the apparatus may use the real-time video display to make sure the visual marker is within the field of view of imaging device. In other cases, particularly but not limited to when mobile apparatus 10 or 30 is configured for autonomous movement, the mobile apparatus may include program instructions for monitoring a real-time display (of which may or may not be visual to a person in the proximity of the mobile apparatus) to determine when a visual marker is within the field of view of imaging device 12.

In particular, program instructions 16 may, in some cases, be configured to detect a variation of color, size and/or depth perception that may be associated with a visual marker. In yet other cases, imaging device 12 may be configured to monitor its view to detect a variation of color, size, or depth perception to detect a visual marker relative to the part of the area/room which it is mounted. In either case, program instructions 16 or the noted program instructions of imaging device 12 may be particularly suitable but are not limited to cases in which the imaging device is arranged on a mobile apparatus to detect a visual marker arranged on a ceiling since there is usually little variation of color or height on a ceiling of an area/room. In any case, as set forth in more detail below, program instructions 16 may additionally or alternatively be for analyzing images received from imaging device 12 and for affecting operations of the apparatus and/or conveying information based on the analyzed images.

In general, the location which imaging device 12 is arranged on mobile apparatuses 10 and 30 may vary among different apparatuses, depending on the anticipated placement of visual markers for which the imaging device will detect and/or image. As set forth in more detail below, visual markers may, in some cases, be arranged on a ceiling, wall or floor of an area/room for the methods disclosed herein. In embodiments in which visual markers are expected to be on the ceiling of an area/room, imaging device 12 may generally be arranged in or on apparatuses 10 and 30 such that the field of view of the imaging device is directed above the apparatus, such as along a surface of mobile apparatuses 10 and 30 facing the ceiling. Alternatively, imaging device 12 may be arranged along a sidewall of mobile apparatus 10 and 30 and angled upward to capture images of a ceiling. In yet other embodiments in which visual markers are expected to be on walls of an area/room, imaging device 12 may generally be arranged in or on apparatuses 10 and 30 such that the field of view of the imaging device is directed sideways from the apparatus. In yet other cases in which visual markers are expected to be on a floor of an area/room, imaging device 12 may generally be arranged along a bottom surface of apparatuses 10 and 30 such that the field of view of the imaging device is directed downward from the apparatus. Alternatively, imaging device 12 may be arranged along a sidewall of mobile apparatus 10 and 30 and angled downward to capture images of a floor.

In general, the field of view and the resolution of imaging device 12 may vary, depending on the applications to which the mobile apparatus 10 and 30 are to be used, the size and clarity of the visual markers they are used to detect as well as the distance of the visual markers relative to the apparatus. An example field of view of imaging device 12 may generally be between 36 $in^2$ and 3.0 $ft^2$, but smaller and larger field of views may be considered. Furthermore, the timing at which imaging device 12 is activated to turn on may vary, depending on the application and/or the design specifications of the mobile apparatus. In some cases, imaging device 12 may be on continuously. In other cases, however, it may be advantageous to operate imaging device 12 less than continuously to conserve power for the mobile apparatus. As such, in some cases, mobile apparatus 10 and/or 30 may be configured to turn on imaging device 12 periodically, i.e., at a set frequency. In yet other cases and as described in more detail below in reference to FIG. 4, mobile apparatuses 10 and 30 may be configured to turn on imaging device 12 upon detecting the apparatus coming to a stop after being in motion. The operation of imaging device 12 upon such activation may be continuous for a set duration, periodic for a set duration, or may be for a time sufficient to create an image.

In addition or alternatively, mobile apparatus 10 and/or 30 may be configured to turn on imaging device 12 upon user input to integrated user interface 20, upon user input to detached user interface 22 or upon activation of a user-activated mechanism on the apparatus (such as but not limited to a mechanism used to lock the position of the apparatus at a particular location in an area/room as described in more detail below). In particular, in accordance with some of program instructions 16, processor 18 may send one or more signals to activate imaging device 12 upon receiving one or signals from user interface 20, from detached user interface 22 or from a user-activated mechanism on the apparatus indicating a user input control/mechanism on one of those interfaces was triggered to turn on imaging device 12. The operation of imaging device 12 upon such activation may be continuous for a set duration, periodic for a set duration, or may be for a time sufficient to create a single image.

In yet other embodiments, mobile apparatuses 10 and 30 may be configured to turn on imaging device 12 upon receipt of a signal from a device independent of mobile apparatuses 10 and 30. More specifically, mobile apparatuses 10 and/or 30 may be equipped with a wireless signal transmitter and/or receiver (e.g., an RF transmitter and/or receiver) to detect signals from a wireless signal transmitter and/or receiver of a device independent of mobile apparatuses 10 and 30. In addition, mobile apparatuses 10 and/or 30 may include program instructions to turn on imaging device 12 upon receipt of such signals. As a consequence, mobile apparatuses 10 and 30 may, in some cases, be configured to turn on imaging device 12 upon detection of a particular device or environment. For example, an entryway to a room may include a wireless signal transmitter and/or receiver and upon passing the wireless signal transmitter and/or receiver, mobile apparatus 10 or 30 may detect signals therefrom which may be used to turn on imaging device 12. Another example is a visual marker having a wireless signal transmitter and/or receiver and upon mobile apparatus 10 or 30 being positioned in view of the wireless signal transmitter and/or receiver, the mobile apparatus may detect signals therefrom which may be used to turn on imaging device 12.

In some embodiments, mobile apparatuses 10 and 30 may be configured to analyze the signals from the independent device to determine whether the device or environment warrants turning on imaging device 12. For example, it may be beneficial to activate imaging device 12 upon detecting mobile apparatus 10 or 30 is entering a patient room or an operating room, but it may be less beneficial to activate imaging device 12 upon detecting mobile apparatus 10 or 30 is exiting a patient room or operating room, entering, or exiting an elevator or is traveling a hallway. In any case, the operation of imaging device 12 upon receipt of a signal from a device independent of mobile apparatuses 10 and 30 may be continuous for a set duration, periodic for a set duration, or may be for a time sufficient to create a single image.

Regardless of the prompt for turning on imaging device 12, the timing and frequency at which imaging device 12 is activated to create an image may vary, depending on the application and/or the design specifications of the mobile apparatus. In some cases, imaging device 12 may be configured to continually produce images when it is turned on. Such a configuration may be particularly suitable if the electronic imaging device of imaging device 12 is a video camera. In other cases, image device 12 may be configured to create images periodically, i.e., at a set frequency. In yet other cases, as shown in FIG. 4 and described in more detail below, mobile apparatuses 10 and 30 may be configured to activate imaging device 12 to create one or more images upon detecting the apparatus coming to a stop after being in motion. In addition or alternatively, mobile apparatus 10 and/or 30 may be configured to activate imaging device 12 to create one or more images upon user input to integrated user interface 20, upon activation of user input to detached user interface 22 or upon activation of a user-activated mechanism on the apparatus (such as but not limited to a mechanism used to lock the position of the apparatus at a particular location in an area/room as described in more detail below).

In yet other embodiments, mobile apparatuses 10 and 30 may be configured to activate imaging device 12 to create one or more images upon receipt of a wireless signal from a device independent of mobile apparatuses 10 and 30. For example, in cases in which mobile apparatus 10 or 30 is positioned in view of a visual marker having a wireless signal transmitter and/or receiver, the mobile apparatus may detect signals therefrom which may be used to activate imaging device 12 to create one or more images. In some embodiments, mobile apparatuses 10 and 30 may be configured to analyze signals from an independent device to determine whether the device or environment warrants imaging device 12 taking an image. In any case, regardless of the prompt for activating imaging device 12 to take an image, the creation of the image/s may be continuous for a set duration, periodic for a set duration, or may be for a single occurrence (i.e., to create a single image).

As noted above, the disclosure provided herein is specific to mobile apparatuses having visual marker detection systems and methods of their use. The visual markers detected by the visual marker detection systems to affect the methods described herein may include any visually identifiable mark, including but not limited to characters (numerical, alphabetical and/or alphanumerical), geometric shapes, symbols, pictorial images as well as linear barcodes and matrix barcodes (e.g., QR codes). In some cases, data embedded marks (i.e., linear barcodes and/or matrix barcodes) may be advantageous for storing information by which to identify the visual marker, storing information by which to operate a mobile apparatus, and/or storing information specific to the location of the data embedded mark. In particular, the mobile apparatuses disclosed herein may be configured to decode images received from an imaging device of the mobile apparatuses to identify visual markers in the received images, determine, and affect operational parameters for the apparatuses, and/or determine and send location-specific information to an information conveying device used in conjunction with the mobile apparatus.

In other cases, the visual markers used in conjunction with the mobile apparatuses described herein for the methods described herein need not include data embedded marks. In particular, the mobile apparatuses disclosed herein may, in some embodiments, include or may be communicably coupled to a database of identifying information, operational parameters, and/or location-specific information which coincide with particular visual markers. In such cases, the mobile apparatuses may include program instructions for accessing information from the database to determine an identity of a visual marker, to determine and affect operating parameters for the mobile apparatus, and/or determine and send location-specific information to an information conveying device used in conjunction with the mobile apparatus based on an image of a particular visual marker.

In yet other embodiments, the mobile apparatuses disclosed herein may not include or be communicably coupled to a database of identifying information, operating parameters, and/or location-specific information. In particular, in some cases, the visual marker detection systems described herein may not be used to identify a visual marker, set operational parameters of a mobile apparatus and/or display location-specific information in relation to the location of the mobile apparatus. Instead, a visual marker detection system may alternatively be used to position a mobile apparatus at a particular location in an area/room. In some cases, a visual marker detection system may alternatively be used to determine and/or verify one or more locations in an area/room at which a mobile apparatus has been arranged. In addition or alternatively, a visual marker detection system may be used to determine and/or verify a mobile apparatus has been suitably positioned at a preset location in an area/room or at a location in proximity to or a preset distance from a device or object in an area/room. Moreover, a visual marker detection system may additionally or alternatively be used to determine whether a mobile apparatus did or did not move to other locations in an area/room in a particular time frame, such as during operation of the apparatus. In some cases, a visual marker detection system may be used for any such functions in addition to being used to identify a visual marker, set operational parameters of a mobile apparatus and/or display location-specific information in relation to the location of the mobile apparatus (regardless of whether the latter functions are facilitated by decoding an image of a visual marker or looking up information in a database correlated with a visual maker).

As noted above, a visual marker may, in some cases, be attached to a ceiling, floor or wall of an area/room. Alternatively, a visual marker may be coupled to a device or object in an area/room. In some of such cases, a visual marker may be coupled to a device or object that is fixedly arranged in an area/room, such as but not limited to a cabinet, door, or window. In yet other cases, a visual marker may be coupled to a device or object which is mobile, such as but not limited to a patient bed, an operating table, or a surgical stand. Reference is made to the definition of the term "mobile" provided herein for configurations which may constitute a device or object mobile and is not reiterated for the sake of brevity. In any case, a visual marker may, in some cases, be suspended from its support surface (i.e., from a ceiling, floor, wall, device or object in an area/room). Alternatively, a visual marker may be coupled directly to its support surface. In either case, the visual marker may include its own substrate on which its visually identifiable mark is arranged. In this manner, the visual marker may, in some cases, be readily detachable from its support surface. Alternatively, a visual marker may be a visually identifiable mark that is integrated into the substrate of the ceiling, flooring, wall, device, or object on which it is arranged.

In any case, a visual marker may, in some cases, be disposed at least approximately 1 foot and, in specific cases, at least approximately 3 feet from an entryway of an area/room. In general, such placement of a visual marker may be advantageous to ensure a mobile apparatus is fully disposed in the area/room when it is positioned within the field of view of the imaging device of the mobile apparatus. In some cases, having a visual marker at least approximately 1 foot and, in specific cases, at least approximately 3 feet from an entryway of an area/room may be particularly advantageous for positioning a mobile room/area disinfection apparatus in the area/room. In particular, as set forth below, a feature common to many area/room disinfection apparatuses is to have configurations to achieve sufficient germicidal efficacy on surfaces greater than 1 meter or even 2 or 3 meters from the disinfection apparatus. As such, having a visual marker at least approximately 1 foot and, in some cases at least approximately 3 feet from an entryway of the area/room may be advantageous to avoid overexposing a space in the area/room in proximity to the door and potentially optimize the extent of the area/room which may be sufficiently disinfected.

In any case, in order to affect its reliability for the methods disclosed herein, the visual marker is configured such that its visually identifiable mark is reasonably distinguishable from its surroundings, i.e., distinguishable from the color and components of the ceiling, flooring, wall, device or object on which the visual marker is arranged. In some cases, a visual marker may include a solid color border around its visually identifiable mark in order to achieve such an objective. In addition or alternatively, the visually identifiable mark may include a distinguishable color relative to the surface to which it is attached. In any case, the size, shape, and clarity of the visual markers may vary among applications, depending on the field of view and resolution of the imaging device on the mobile apparatus. In some cases, it may be advantageous for the visual markers to be relatively small, such as having an areal dimension less than approximately 100 $in^2$ and, in some cases, less than approximately 30 $in^2$ or even less than approximately 5 $in^2$ i.e., if the imaging device can adequately create an image of sufficient resolution to be analyzed and/or decoded by the program instructions of the mobile apparatus. In particular, smaller visual markers may be less distracting in a room.

As noted above, methods are disclosed herein that utilize visual marker detection systems to determine and/or verify one or more locations in an area/room at which a mobile apparatus has been arranged. The one or more locations may be referenced as fixed locations in an area/room (i.e., within a particular x-y coordinate region in the area/room or at a particular x-y coordinate point in the area/room) or may be referenced as locations relative to other devices or objects in an area/room. For example, regarding the latter scenario, it may, in some cases, be advantageous to determine and/or verify a location of a mobile disinfection apparatus relative to a high-touch device, a high-touch object, or a device or object in a room suspected to be contaminated with pathogenic microorganisms. As used herein, the terms "high-touch device" and "high-touch object" refer to devices and objects that are frequently touched, handled, or occupied. Examples of high-touch devices and high-touch objects which may be found in an area/room include but are not limited to desktops, keyboards, telephones, chairs, tables, door and cabinet handles, light switches, and sinks. Examples of high-touch devices and high-touch objects and/or devices in a healthcare setting include but are not limited to patient beds, bedside tables, tray tables, operating tables, surgical stands, intravenous poles, and wheelchairs.

In some cases, it may, in some cases, be advantageous to determine and/or verify a location of a mobile disinfection apparatus relative to a particular side of such devices or objects. As used herein, determining and/or verifying a location of a mobile apparatus relative to another device or object in an area/room refers to determining and/or verifying the apparatus being in close proximity to (i.e., within 3 feet) or a set distance range from the device or object and, in some cases, in close proximity to or a set distance from a particular side of the device or object. For instance, a mobile disinfection apparatus in a patient room may be determined to be in proximity to or a set distance from a bed and, in some cases, in proximity or a set distance from a particular side of the bed.

As noted above, a visual marker may be coupled to a device or an object in an area/room and the device or the object may be fixedly arranged in the room or may be mobile. In some cases, a visual marker may be coupled to a device or an object that is of interest to determine and/or verify the relative location of a mobile apparatus, such as a high-touch device, a high-touch object or a device or object that is prone to be contaminated with pathogenic microorganisms. Alternatively, a process of determining and/or verifying the location of a mobile apparatus relative to a fixed or moveable device or object in an area/room need not be limited to having a visual marker attached to the device or object. In particular, the determination and/or verification of the location of a mobile apparatus in an area/room may depend on a known or presumed location of a device or object in the area/room, which may be correlated to a location of a visual marker in the area/room (regardless of what surface the visual marker is attached). For example, a patient room may have a predetermined layout of its furniture and equipment, including but not limited to having a particular location for a patient bed to be disposed. As such, although the patient bed may include wheels for easing movement of the bed, the patient bed may be referenced for a location of mobile apparatus in the area/room based on the predetermined location that the patient bed is to be disposed in the area/room.

In general, determining and/or verifying the location of a mobile apparatus in an area/room relative to a device or an object in an area/room may be advantageous for denoting that the apparatus has been placed at a location which the device or object may particularly benefit from an operation conducted by the apparatus. For instance, in cases in which a mobile disinfection apparatus projects a germicide exterior to the apparatus, it may be advantageous to determine and/or verify the location of the mobile disinfection apparatus relative to a device or object in an area/room to denote at least a side of the device or object facing the mobile disinfection apparatus will be or has been subjected to a disinfection process performed by the apparatus. In addition, in cases in which a mobile disinfection apparatus generates a germicide interior to the apparatus to disinfect air routed therethrough from the ambient of the apparatus, it may be advantageous to determine and/or verify the location of the mobile disinfection apparatus relative to a device or object to denote the air in a region in proximity to at least a side of the structure will be or has been subjected to a disinfection process performed by the apparatus.

In some cases, it may be advantageous to position a mobile apparatus within a set distance range from a device or object in an area/room. For example, in embodiments in which a mobile disinfection apparatus discharges a germicide into its ambient, the efficacy of the germicide on a surface is generally dependent on the distance the surface is from the mobile disinfection apparatus. As such, it may be advantageous to position the mobile disinfection apparatus within a distance which the apparatus is known to achieve a particular reduction of bacterial contamination within a particular exposure time. For instance, it may be advantageous to position a mobile disinfection apparatus a distance of less than approximately 2 feet from a device or object.

In some further cases, it may be advantageous to specify a lower end of the distance range in order to optimize the amount of surface area of the device or object disinfected by the apparatus. In particular, in some disinfection apparatuses, such as those which project germicidal light, the areal coverage of the germicide emitted from the apparatus increases as it is projected from the device. For such scenarios, an example distance range to position a mobile disinfection apparatus from an object or device for the methods disclosed herein may be between approximately 1 foot and approximately 2 feet, but smaller or larger ranges and/or smaller or larger range end points may be considered. In some cases, a visual marker may be arranged in a room a set distance from a device or object of interest (or from a presumed position of the device or object) in order to enable a mobile apparatus to be positioned within a set distance range from the device or object. Alternatively, a visual marker may be arranged on the device or object of interest. In such cases, the mobile apparatus may include a distance sensor and/or program instructions which analyze the size and/or clarity of the visual marker in an image and correlate them to a distance.

In embodiments in which determining or verifying a mobile apparatus at a fixed location in an area/room (i.e., within a particular x-y coordinate region in the area/room or at a particular x-y coordinate point in the area/room) is desired, it may be advantageous to have a visual marker arranged on or suspended from a ceiling of the area/room or arranged on a floor of the area/room. In particular, having a visual marker in such locations may aid in verifying a position of a mobile apparatus within an x-y coordinate region or at a particular x-y coordinate point in an area/room without the need for a distance sensor or image clarity or size analysis to be used in conjunction with the imaging device of the mobile apparatus. More specifically, detecting a visual marker arranged on or suspended from a ceiling of an area/room or arranged on a floor of an area/room will inherently define an x-y coordinate region of an area/room characterized by the field of view of the imaging device on the mobile apparatus since the vertical distance between the visual marker and imaging device will not vary (i.e., presuming the elevation of the ceiling and floor across the area/room does not substantially change).

Conversely, detecting a visual marker that is arranged along a wall of an area/room or is arranged along a sidewall of a fixed or moveable structure in an area/room will only have one dimension of an x-y coordinate region of an area/room characterized by the field of view of the imaging device on the mobile apparatus since the distance between the visual marker and imaging device may vary. In such scenarios, the other dimension of the x-y coordinate region of an area/room (i.e., the distance of the mobile apparatus relative to the visual marker) may be assumed or, alternatively, may be determined by a distance sensor disposed on the mobile apparatus or via program instructions which analyze the size and/or clarity of the visual marker in an image. Furthermore, although a mobile apparatus may not need a distance sensor and/or such program instructions to analyze the size and/or clarity of the visual marker in an image, particularly when used in conjunction with a visual marker arranged or suspended from a ceiling of an area/room or arranged on a floor of an area/room, a mobile apparatus may include such provisions for other purposes.

As noted above, the apparatuses and methods disclosed herein are emphasized in reference to mobile disinfection apparatuses and, more specifically, in reference to area/room disinfection apparatuses and methods for disinfecting an area/room. As such, mobile disinfection apparatus 30 of FIG. 2 includes germicidal source 32 arranged such that germicide 34 is projected into an ambient of apparatus 30 (i.e., exterior to apparatus 30). It is noted that the mobile area/room disinfection apparatuses considered herein are not limited to apparatuses having a germicidal source extending beyond a support structure of the application and/or having a germicidal source arranged along the upper surface of a support structure. In particular, a mobile area/room disinfection apparatus considered herein may, in some embodiments, have a germicidal source arranged partially or wholly inset to a structure of the apparatus with an opening or transparent window to allow the transmission of a germicide generated therefrom to be projected into an ambient of the mobile apparatus. In addition, a mobile area/room disinfection apparatus considered herein may have a germicidal source arranged along any portion of the apparatus, including the top portion, sidewall portions or the bottom of the apparatus. In yet other cases, the mobile disinfection apparatuses considered for the methods disclosed herein need not project a germicide into their ambient or even be configured to do so. For instance, a mobile disinfection apparatus which is configured to draw in air, disinfect the air internal to the apparatus and project the disinfected air back into the room/area in which the mobile disinfection apparatus is arranged may be considered for the methods disclosed herein.

The germicidal sources considered herein for the mobile disinfection apparatuses disclosed therein may be any device configured to generate a dispersible germicide (regardless of whether the mobile disinfection apparatus is configured to disperse the germicide exterior to the apparatus or internal to the apparatus). In particular, the germicidal sources considered herein may be any device or apparatus configured to generate a germicide in form of a liquid, a vapor, a gas, a plasma, or germicidal light. Examples of germicidal sources which may be configured to disperse liquid, vapor, gaseous, or plasma germicides include but are not necessarily limited to liquid sprayers, foggers, plasmas torchers and misting systems including wet and dry mist systems. As used herein, the term "mist" refers to a suspension of minute globules of a liquid in a gas. For use herein, a germicidal mist is categorized as a liquid germicide. In some cases, a germicidal source may be configured to generate more than one type of germicide. For example, some germicidal light sources may produce intense heat and/or ozone which have a germicidal effect. In any case, the mobile disinfection apparatuses described herein may include any number of germicidal sources, depending on the design specifications of the disinfection apparatus. Furthermore, in cases in which a mobile disinfection apparatus includes multiple germicidal sources, the multiple germicidal sources may be configured to generate the same or different germicides.

As used herein, the term "germicide" refers to an agent for deactivating or killing microorganisms, particularly disease carrying and/or disease producing microorganisms (a.k.a., germs). The term "kill," as used herein, means to cause the death of an organism. In contrast, the term "deactivate," as used herein, means to render an organism unable to reproduce without killing. As such, a germicide which is configured to deactivate a microorganism, as used herein, refers to an agent which renders a microorganism unable to reproduce but leaves the organism alive. Furthermore, the term "germicidal source" as used herein refers to a collection of one or more components used to generate and disperse a germicide. In some embodiments, a germicidal source may include components in addition to the component/s used to generate the germicide to affect the dispersal of the germicide from the generation component/s.

In some cases, the disinfection devices considered herein may, in some embodiments, include a germicidal source configured to generate a liquid, vapor, gaseous or plasma germicide which imparts its deactivation or killing functionality by the manner in which it is used. In other cases, a germicidal source of the mobile disinfection apparatuses described herein may be configured to generate a liquid, vapor, gaseous or plasma germicide that is molecularly configured to deactivate and/or kill microorganisms. As used herein, the phrase "molecularly configured" refers to the elemental composition of a substance (i.e., the number and type of atoms making up a substance) to impart the function stated after the phrase. In some embodiments, the functionality of a liquid, vapor, gaseous or plasma germicide to deactivate and/or kill a microorganism may be attributed to the elements constituting the germicide and, thus, such germicides may be referenced as being molecularly configured to deactivate and/or kill microorganisms. This is in contrast to liquid, vapor, gaseous or plasma germicides which impart their deactivation and/or killing functionality by the manner in which they are used.

For example, boiling water and steam are often effective sterilizing agents due to the temperature at which they are employed rather than their molecular composition. An example of a gaseous germicide which deactivates or kills microorganisms by the manner in which it is used is air at a very high temperature. Furthermore, the germicidal effectiveness of some plasma germicides is primarily due to the presence and activity of charged particles making up the plasma rather than the molecular composition of the charged particles. An example of a gaseous germicide that is molecularly configured to kill microorganisms is ozone. Examples of plasmas germicides that are molecularly configured to deactivate or kill microorganisms are those that employ or generate reactive oxygen species. Examples of liquid and vapor germicides that are molecularly configured to deactivate or kill microorganisms include liquid and vapor disinfection solutions having a principal disinfection agent such as but not limited to bleach, hydrogen peroxide, chlorine, alcohol, quaternary ammonium compounds or ozone. In any of such cases, the liquid and vapor germicides may be aqueous or non-aqueous.

As noted above, a germicidal source of the mobile disinfection apparatuses described herein may, in some embodiments, be a source configured to generate germicidal light. The term "germicidal light" refers to light which is capable of deactivating or killing microorganisms, particularly disease carrying and/or disease producing microorganisms (a.k.a., germs). Ranges of light which are known to be germicidal include ultraviolet B (UVB) and ultraviolet C (UV-C) light, particularly ultraviolet light between approximately 200 nm and approximately 320 nm, and more particularly ultraviolet light at 220 nm and ultraviolet light between 260 nm and 265 nm. Another range of light which is known to be germicidal includes visible violet-blue light (also known as high-intensity narrow-spectrum (HINS) light) between approximately 400 nm and approximately 470 nm, and particularly at 405 nm. The germicidal sources considered for the mobile disinfection apparatuses disclosed herein may be configured to generate any one or more of such ranges or wavelengths of germicidal light.

In some embodiments, a germicidal light source of the mobile disinfection apparatuses considered herein may generate ranges of light which are not germicidal such as but not limited to visible light greater than approximately 500 nm, but such capability will not deter from the reference of the light source being germicidal. To that regard, a light source or lamp of the mobile apparatuses disclosed herein may, in some cases, be characterized in the type of light it generates, but such characterization need not limit the light source or lamp to generating only that type of light. For example, an ultraviolet lamp is one which generates ultraviolet light, but it may produce light of other wavelengths. In any case, the germicidal light sources considered for the mobile disinfection apparatuses described herein may be of any size and shape, depending on the design specifications of the disinfection apparatuses. The terms "germicidal light source" and "germicidal lamp" are used interchangeably herein and refer to a collection of one or more components used to generate and disperse germicidal light.

Examples of germicidal light sources which may be configured to generate ultraviolet light and/or HINS light include discharge lamps, light emitting diode (LED) solid state devices, and excimer lasers. HINS lamps are generally constructed of LEDs. A discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the discharge lamps which may be considered for the germicidal sources described herein include gas-discharge lamps as well as surface-discharge lamps.

Discharge lamps may be further characterized by the type of gas/es employed and the pressure at which they are operated. The discharge lamps which may be considered for the germicidal sources described herein may include those of low pressure, medium pressure, and high intensity. In addition, the gas/es employed may include helium, neon, argon, krypton, xenon, nitrogen, oxygen, hydrogen, water vapor, carbon dioxide, mercury vapor, sodium vapor and any combination thereof. In some embodiments, various additives and/or other substances may be included in the gas/es. In any case, the discharge lamps considered for the germicidal sources described herein may include those which generate continuous light and those which generate light in short durations, the latter of which are often referred to as flashtubes or flashlamps. Flashtubes or flashlamps that are used to supply recurrent pulses of light are often referred to as pulsed light sources.

A commonly used gas-discharge lamp used to produce continuous light is a mercury-vapor lamp, which may be considered for the mobile disinfection apparatuses described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the mobile disinfection apparatuses described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and killing of microorganisms.

Although they are not readily available on the commercial market to date, a surface-discharge lamp may be considered for the mobile disinfection apparatuses described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp, and a surface discharge lamp in no way restrict the disinfection devices described herein to include such lamps. Rather, the aforementioned descriptions and comparisons are merely provided to offer factors which one skilled in the art may contemplate when selecting a germicidal light source for the mobile disinfection apparatuses described herein.

As noted above, in some cases, the germicidal light source may be an excimer laser and, thus, the germicidal light projected into an ambient of the mobile disinfection apparatuses disclosed herein may be a narrow beam of light. In some cases, a mobile disinfection apparatus having a laser may be configured to move the laser and/or the apparatus may be configured to move itself during a disinfection cycle such that multiple surfaces may be disinfected by the laser. The mobile disinfection apparatus may be of any shape, size, or configuration in which to achieve such an objective.

As set forth above, the apparatuses and methods disclosed herein may, in some cases, be specific to mobile area/room disinfection apparatuses and methods for disinfecting an area/room. More specifically, the mobile apparatuses disclosed herein, including with respect to the mobile apparatuses used in the methods disclosed herein, may have configurations which facilitate area/room disinfection. As used herein, the term "area/room disinfection apparatus" refers to an apparatus configured to disinfect a space which is suitable for human occupancy so as to deactivate, destroy or prevent the growth of disease-carrying microorganisms in the area. As used herein, the terms "area/room disinfection apparatus", "area disinfection apparatus" and "room disinfection apparatus" may be used interchangeably herein. Although some mobile disinfection apparatuses considered herein and used for the methods described herein may be configured for area/room disinfection, the apparatuses and methods need not be so limited. Furthermore, a mobile disinfection apparatus considered herein and used in the methods described herein need not include all or any of the features described below that are generally associated with area/room disinfection apparatuses.

In general, an area/room disinfection apparatus includes configurations to distribute an effective amount of germicide in a spacious manner to an ambient of an area/room in which the apparatus is arranged to maximize the number of surfaces and objects disinfected in the area/room. The apparatus may be of any shape, size, or configuration to achieve such an objective. An example configuration of an area/room disinfection apparatus which may be particularly considered for the mobile disinfection apparatuses discussed herein is to be configured to direct a germicide to a region approximately 2 feet and approximately 4 feet from a floor of an area/room in which the apparatus is arranged. In particular, the region between approximately 2 feet and approximately 4 feet from a floor of a room is considered a "high touch" region of an area/room since objects of frequent use are generally placed in such a region. Examples of configurations which offer such germicide direction are disclosed in U.S. patent application Ser. No. 13/706,926 filed Dec. 6, 2012 and Ser. No. 13/708,208 filed Dec. 7, 2012 and International Patent Application No. PCT/US2014/059698 filed Oct. 8, 2014, all of which are incorporated herein by reference as if set forth fully herein. Other features specific to area/room disinfection apparatuses are disclosed in such documents as well. For example, other features of area/room disinfection apparatuses include wheels and/or a handle to affect portability for the apparatuses. In addition, many area/room disinfection apparatuses include configurations for remotely starting the apparatuses such that individuals need not be present in the area/room when operation of the apparatus commences.

Another feature of an area/room disinfection apparatus which may be included in the mobile disinfection apparatuses considered herein is to include configurations to distribute an effective amount of germicide to achieve at least a 2-log reduction in bacterial contamination on surfaces that are greater than 1 meter or even 2 or 3 meters from its germicidal source/s. Configurations used to generate such an effect generally depend on the configuration of the germicidal source/s, particularly the size of the germicidal source/s, the intensity and/or frequency at which the germicide is dispersed and/or the orientation of the germicidal source/s in the apparatus. In general, the germicidal sources considered herein may be any shape, size, orientation, and configuration and may be conducted at parameters to achieve a desired reduction in bacterial contamination on surfaces that are greater than 1 meter or even 2 or 3 meters from the apparatus. An example of an orientation of germicidal source/s which may aid in achieving such an effect is that the germicidal source/s may be vertically arranged (e.g., the germicidal source/s are arranged lengthwise substantially perpendicular to a horizontal plane of the apparatus) to aid in distributing the germicide greater distances within an area/room. Moreover, in cases in which an area/room disinfection apparatus includes one or more germicidal light sources, power fluxes of at least 1.0 W/m$^2$ may be generally used to achieve at least a 2-log reduction in bacterial contamination on surfaces within an area/room that are greater than 1 meter from the germicidal light source/s.

Furthermore, another feature common to area/room disinfection apparatuses which the some of the mobile disinfection apparatuses described herein may include is one or more actuators for moving its germicidal source/s with respect to other components of the apparatus (such as a base of the apparatus or a support structure supporting the germicidal source/s and/or actuator) to aid in the distribution of the germicide in an area/room. In such cases, a germicidal source may be moved in vertical, horizontal, and/or diagonal directions via the one or more actuators. It is noted that the configuration of an area/room disinfection apparatus to move one or more of its germicidal sources may include configurations to induce 360° distribution of a germicide around the apparatus as described below, but the apparatuses disclosed herein are not necessarily so limited. In particular, the area/room disinfection apparatuses disclosed herein may include configurations to induce any distribution of a germicide, including those which induce a distribution less than 360° around the apparatus. In some cases, the area/room disinfection apparatuses disclosed herein may include processor-executable program instructions for activating one or more of the actuator/s to move the germicidal source relative to other components of the apparatus while the germicidal source is emitting a germicide and also in between projections of the germicide in cases in which a pulsed germicidal source is used.

Another feature of an area/room disinfection apparatus which may be included in the mobile disinfection apparatuses considered herein is a configuration to distribute a germicide 360° around the apparatus. For example, in some cases, the arrangement of one or more germicidal sources in a mobile disinfection apparatus may be such that a germicide emitted from the germicidal source/s is projected approximately 360° around the apparatus. For instance and as is shown by germicidal source 32 in FIG. 2, a mobile disinfection apparatus may, in some cases, include a single germicidal source that is arranged to distribute a germicide approximately 360° around the apparatus. In other cases, a mobile disinfection apparatus may include a plurality of germicidal sources that are arranged to collectively distribute a germicide approximately 360° around the apparatus. In either case, the mobile disinfection apparatuses may be void of germicide-blocking components approximately 360° around their germicidal source/s such that the germicide emitted from the germicidal source/s substantially encircles the apparatus.

In additional or alternative cases, a mobile disinfection apparatus considered herein may be configured to move one or more of its germicidal source/s and/or one or more of its other components to distribute a germicide approximately 360° around the apparatus. For instance, in some cases, a mobile disinfection apparatus may include one or more moveable germicidal sources (such as but not limited to a sprayer or laser) that are configured to move to distribute a germicide 360° around the apparatus. In other cases, a mobile disinfection apparatus may include a moveable housing around one or more of its germicidal sources, wherein the housing that has one or more openings or one or more transparent windows to transmit a germicide from the germicidal source/s to an exterior of the apparatus. In such cases, the housing and, in some cases, the germicidal source/s may be moved to achieve a 360° distribution of germicide around the apparatus through the openings and/or holes of the housing. In yet other cases, particularly in scenarios in which a mobile disinfection apparatus includes a germicidal light source, the mobile disinfection apparatus may include a reflector to help distribute germicidal light 360° around the apparatus. In such cases, the reflector may be stationary or, alternatively, may be configured to move to achieve the 360° distribution of the germicide light.

Another component which is often used in conjunction with area/room disinfection apparatuses which may be considered for the disinfection apparatuses described herein is a movement detection sensor and/or an area/room occupancy sensor, such as a motion sensor, a thermal sensor, a Doppler sensor, or a photo recognition sensor. In particular, to prevent inadvertent exposure of a germicide to individuals during disinfection of an area/room, the disinfection apparatuses considered herein may include program instructions to inhibit or terminate activation of a power supply circuit to the germicidal source upon detecting movement and/or occupancy in the area/room in which the apparatus is arranged. One or more movement detector sensors and/or one or more occupancy sensors may be integrated into an area/room disinfection apparatus and/or may be remote from an area/room disinfection apparatus, the latter of which may be electrical communication with the area/room disinfection apparatus via wired or wireless connections. A benefit of a movement sensor or occupancy sensor being remote from an area/room disinfection apparatus is that it may be positioned closer to any area of interest for monitoring movement and/or occupancy, such as near an entryway of an area/room. A benefit of having a movement sensor or occupancy sensor integrated into an area/room disinfection apparatus is that it cannot be misplaced, however, such a benefit may be provided in a remote sensor by tethering it to the area/room disinfection apparatus. In any case, a movement sensor or an occupancy sensor used in conjunction with a disinfection apparatus may, in some cases, be repositionable such that its field of coverage is directed to a particular area of interest.

An example of a movement sensor which may be particularly beneficial to use in conjunction with an area/room disinfection apparatus is a door movement sensor. In particular, a door movement sensor may be used to monitor movement of a door to a room in which an area/room disinfection apparatus is arranged for a disinfection process. The door movement sensor may be integrated into the area/room disinfection apparatus and/or may be remote from the area/room disinfection apparatus. In the latter of such embodiments, the door movement sensor may be used inside or outside of the room in which the area/room disinfection apparatus is arranged. Also, a remote door movement sensor may be one which is configured to be placed in contact with a door for detecting its movement or may be one which may be remote from a door for detecting its movement. Regardless of whether a door movement sensor is integrated or remote from an area/room disinfection apparatus, a door movement sensor may be used as the sole sensor of an area/room disinfection apparatus for detecting movement/occupancy in a room or may be used in addition to one or more other movement sensors and/or occupancy sensors which may be integrated or remote from the area/room disinfection apparatus. As an example, FIG. 2 shows mobile apparatus 30 in electrical communication with remote door movement sensor 39, but it is noted that the disinfection apparatuses disclosed herein are not restricted to such a configuration.

Yet another feature which may be included in the mobile apparatuses described herein to specifically affect room/area disinfection is processor executable program instructions for receiving data regarding characteristics of an area/room in which the mobile disinfection apparatus is to be operated. In general, the phrase "characteristics of an area/room" as used herein refers to physical attributes as well as non-physical attributes of an area/room. Non-physical attributes of an area/room include but are not necessarily limited to identifiers used to reference an area/room (e.g., room number and/or room name) and occupancy information regarding an area/room (e.g., infection information of a patient previously occupying the space, or a patient scheduled to occupy the space). Physical attributes of an area/room include but are not necessarily limited to size and/or dimensions of the area/room and/or the number, size, distances, locations, reflectivity and/or identification of surfaces, objects and/or items within the area/room. In some cases, a physical attribute of an area/room may be the identification of one or more pathological organisms and, sometimes further the number or concentration of such organism/s in the area/room, in a particular region of the area/room, or on a particular surface in the area/room.

In any case, the data received regarding the characteristics of the area/room in which the mobile disinfection apparatus is to be operated may be utilized in a number of manners, including but not limited to recordation or reporting purposes or setting one or more operational parameters of the apparatus. In some cases, the mobile apparatuses described herein may include one or more sensors for detecting and/or mapping physical characteristics of an area/room and such information may be used for recordation and/or to affect operation of the apparatus. In additional or alternative cases, the mobile apparatuses described herein may be programmed to access physical characteristics of an area/room from a database communicably coupled to the apparatus. For example, a preassigned room identifier (such as "103" or "Operating Room") may be entered into an apparatus (such as by key entry at a user interface, scanning a barcode or receiving a wireless signal upon entry into the area/room) and one or more physical characteristics and, in some cases, a map or model of the area/room may be accessed from a database outlining such correlative information. As noted above, the apparatuses described herein may, in some cases, include means for automatically moving the apparatus. In some such cases, the apparatus may include program instructions to move the apparatus in accordance with characteristics of an area/room. Examples of area/room disinfection apparatuses with some of the aforementioned program instructions are disclosed in U.S. application Ser. No. 13/706,926 filed Dec. 6, 2012, which is incorporated by reference as if set forth fully herein.

As noted above, several examples of program instructions 16 for operating the apparatuses presented herein are described in reference to FIGS. 3-12. More specifically, FIGS. 3-12 illustrate flowcharts of methods for utilizing mobile apparatuses having visual marker detection systems. Although the methods and apparatuses described in reference to FIGS. 3-12 below are specific to disinfection methods and apparatuses for disinfecting an area/room, the methods and apparatuses described in reference to FIGS. 3-12 are not necessarily limited to disinfection apparatuses and the processes described in reference to the methods are not necessarily limited to disinfecting an area/room. On the contrary, it is contemplated that the processes and apparatus features disclosed in reference to FIGS. 3-12 may be applied to any mobile apparatus constituted by any one or more of the provisions described above for a mobile apparatus as referred to herein. As such, the mobile apparatuses referenced in FIGS. 3-12 may include any configuration of mobile apparatuses 10 and/or 30 described in reference to FIGS. 1 and 2. Furthermore, the designated visual markers referenced in FIGS. 3-12 may include any type and configuration of a visual marker as described above. Moreover, it is noted that the processes described in reference to FIGS. 3-12 are not necessarily mutually exclusive to the flow of program instructions depicted in those figures. Furthermore, any of the program instructions described in reference to FIGS. 3-12 may be used in conjunction with each other.

Turning to FIG. 3, a flowchart is shown including block 50 which denotes positioning a mobile disinfection apparatus in an area/room such that a designated visual marker disposed in the area/room is within a field of view of an imaging device of the mobile disinfection apparatus. The positioning of a mobile disinfection apparatus may be manual or automated, the latter of which may be accomplished by user input controls (i.e., at the apparatus or via remote control) or by autonomous movement of the mobile disinfection apparatus. In embodiments in which positioning the mobile disinfection apparatus is autonomous, the positioning step may be accomplished by following a programmed path or by traveling via navigational controls of the mobile disinfection apparatus. As noted above, the blocks of steps outlined in the flowchart of FIG. 3 may, in some embodiments, represent program instructions which a mobile apparatus described herein may include. As such, block 50 in FIG. 3 may refer to program instructions for automatically positioning a mobile disinfection apparatus. In other cases, however, the block of steps outlined in the flowchart of FIG. 3 may represent processes performed by a user of a mobile disinfection apparatus. In such cases, block 50 in FIG. 3 may refer to a user of a mobile apparatus positioning the disinfection apparatus manually or by user input controls (i.e., at the apparatus or via remote control).

In any case, as noted above, the visual marker referenced in block 50 of FIG. 3 is a designated visual marker. As used herein, a "designated visual marker" refers to a visual marker which is preselected and/or that is associated with a particular mobile apparatus. As such, the process denoted in block 50 may, in some cases, be specific to positioning a mobile disinfection apparatus in an area/room such that a preselected visual marker in the area/room is within a field of view of an imaging device of the disinfection apparatus. In some of such cases, the process may include a user selecting a visual marker in an area/room and then positioning a mobile disinfection apparatus such that the visual marker is within a field of view of an imaging device of the disinfection apparatus. In such cases, the positioning of the disinfection apparatus may be done manually or by user input controls (i.e., at the apparatus or via remote control). In yet other cases, a user of a mobile disinfection apparatus may select a visual marker via a user interface of the apparatus and the apparatus may move itself in accordance with program instructions associated with the preselected visual marker. Alternatively, a visual marker to which a mobile disinfection apparatus is to be positioned relative to may be preselected by a different entity (i.e., different from a user of the apparatus, such as but not limited to a different person, a computer program that is on the mobile disinfection apparatus, or computer program that is independent of the mobile disinfection apparatus). In such cases, the preselected visual marker may be communicated to the user via a user interface of the mobile apparatus or may be communicated to the mobile apparatus to affect program instructions associated with the preselected visual marker to move apparatus.

In any case, the preselection may be by choice or may be determined by one or more factors related to the need or the desire for a disinfection process to be performed in the area/room (such as but not limited to the amount of time since the room/area was last disinfected, a disinfection schedule for the room/area, patient discharge status of the area/room and/or pathogen diagnosis of previous occupants). Choosing a visual marker to position a mobile apparatus relative to includes a user scanning an area/room and selecting a visual marker or alternatively a choosing a visual marker from a listing or map of visual markers for an area/room, floor, or building. In yet other cases, choosing a visual marker may involve choosing a room in which to have a disinfection process performed, particularly by inputting or selecting room identifying information on a user interface of a mobile disinfection apparatus or in a computer database communicably coupled to the mobile disinfection apparatus or by detecting entry of a mobile disinfection device into the area/room. In such cases, the mobile disinfection apparatus may include navigational program instructions to position the apparatus relative to a particular visual marker associated with the room identifying information, specifically such that the visual marker is within the field of view of the imaging device of the mobile apparatus.

In addition or alternatively, the process denoted in block 50 may be specific to positioning a mobile disinfection apparatus in an area/room such that a visual marker which is associated with the mobile disinfection apparatus is within a field of view of an imaging device of the disinfection apparatus. As used herein, the phrase "associated with a mobile apparatus" refers to an alliance between a mobile apparatus and a noted element, wherein the noted element has a means for detecting the mobile apparatus and/or the mobile apparatus has a means for detecting or identifying the noted element or a means for detecting or identifying a classification to which the noted element belongs to determine whether the noted element is one of a select group of one or more elements linked to the mobile apparatus. As such, "a visual marker associated with a mobile apparatus" may refer to a visual marker that is linked with a mobile apparatus that has a means for detecting or identifying the visual marker or a classification thereof. In addition or alternatively, "a visual marker associated with a mobile apparatus" may refer to a visual marker that has a means for detecting a mobile apparatus that is linked to the visual marker.

As discussed in more detail below, a means for detecting or identifying a visual marker or a classification to which a visual marker belongs may, in some cases, include program instructions for analyzing an image of the visual marker taken by the imaging device of the mobile apparatus. In other cases, a means for detecting or identifying a visual marker or a classification to which a visual marker belongs may be a configuration of an imaging device of a mobile apparatus to monitor its view to detect a variation of color, size, or depth perception to detect a visual marker relative to the part of the area/room which it is mounted. In yet other cases, a mobile apparatus may include a wireless signal receiver, such as an infrared receiver or a radio frequency receiver, for detecting and/or identifying a visual marker having a corresponding wireless signal transmitter. Conversely, a visual marker may include a wireless signal receiver or a wireless transceiver for detecting a signal transmitted from a mobile apparatus passing in vicinity of the visual marker. In yet other cases, a visual marker may not include a wireless transmitter, a wireless receiver, or a wireless transceiver.

In some cases, a wireless transmitter, receiver, or transceiver of a visual marker and/or of a mobile apparatus may be configured to send and/or receive signals of wavelengths that are particular to an association between the mobile apparatus and the visual marker. In this manner, the detection of the signals between the mobile apparatus and visual marker may be indicative of an association therebetween. In yet other cases, a wireless transmitter, receiver, or transceiver of a mobile apparatus or of a visual marker may not be configured to send and receive signals that are particularly indicative of an association therebetween. In such cases, the signal transmissions may simply be used to determine when a mobile apparatus has been positioned in a vicinity of a visual marker and the mobile apparatus may include program instructions for analyzing an image of the visual marker to determine whether the visual marker is associated with the mobile apparatus. In either of such scenarios, a visual marker may, in some cases, include one or more visual or audible indicators which may be activated upon detecting a signal from a mobile apparatus. Alternatively, a mobile apparatus may, in some cases, include one or more visual or audible indicators which are activated upon detecting a signal from a visual marker. In general, the visual and/or audible indicators may include any changeable indicator known in the art, such as but not limited to a lighted bulb, an audible alarm and/or a visual display, the latter of which may include but is not limited to text on a graphical user interface.

In some cases, visual and/or audible indicator/s of a visual marker and/or a mobile apparatus may serve to indicate when the mobile apparatus has been positioned in the vicinity of the visual marker and, in specific cases, serve to indicate when the mobile apparatus has been positioned such that the visual marker is within a field of view of an imaging device of the disinfection apparatus. For example, a user positioning the mobile apparatus (either manually or by user input controls (i.e., at the apparatus or via remote control)) may utilize the one or more visual and/or audible indicators to know when the mobile apparatus has been positioned in the vicinity of the visual marker and, in specific cases, to know when the mobile apparatus has been positioned such that the visual marker is within a field of view of an imaging device of the disinfection apparatus. In addition or alternatively, a mobile apparatus may be programmed to detect when a visual or audible indicator is activated on a visual marker to know when the mobile apparatus has been positioned in the vicinity of the visual marker and, in specific cases, to know when the mobile apparatus has been positioned such that the visual marker is within a field of view of an imaging device of the disinfection apparatus. In yet other cases, a visual marker may not include visual and/or audible indicators.

As set forth above, a means for detecting or identifying a visual marker or a classification to which a visual marker belongs may vary among different mobile disinfection apparatuses, including but not limited to program instructions for analyzing an image of the visual marker taken by imaging device of the mobile apparatus. In any case, regardless of whether a mobile apparatus is used to analyze an image of a visual marker to determine whether the visual marker is associated with the mobile apparatus, an image of the visual marker may be analyzed for other purposes as described in more detail below in reference to FIGS. 6-11. In particular, a mobile apparatus may be configured to analyze an image of a visual marker to determine whether the mobile apparatus is properly positioned relative to the visual marker, determine whether the visual marker is different from a visual marker of a previous image, set operational parameters of the mobile disinfection apparatus for a disinfection cycle and/or communicate location specific information.

As noted above, the process denoted in block 50 of FIG. 3 is specific to positioning a mobile disinfection apparatus such that a designated visual marker is within a field of view of an imaging device of the apparatus. In some cases, the process may involve monitoring what the imaging device is viewing in real-time in order to determine when the visual marker is within its field of view. In some of such cases, the monitoring may be done by a person moving the mobile disinfection apparatus (i.e., manually or by user input controls (i.e., at the apparatus or via remote control)), particularly monitoring the view of the imaging device via a display on an integrated or detached user interface of the apparatus. In other cases, the mobile disinfection apparatus or its imaging device may include program instructions to monitor what the imaging device is viewing in real-time while the disinfection apparatus is being moved (i.e., by a user of the apparatus or by automated movement).

Alternatively, in cases in which a mobile apparatus includes a wireless transmitter, receiver or transceiver, the wireless device may be configured to transmit or receive signals in a region only with respect to the field of view of the imaging device and, thus, detection of any of such signals will be indicative that a designated visual marker is within a field of view of the imaging device. In yet other cases, a mobile apparatus may include a wireless transmitter, receiver, or transceiver that is configured to transmit or receive signals in a region outside or larger than the field of view of the imaging device. As a result, detection of any of such signals will simply indicate a mobile disinfection apparatus is in the vicinity of a designated visual marker, but not necessarily having the visual marker within a field of view of the imaging device. In such cases, subsequent to the detection that the mobile disinfection apparatus is in vicinity of the visual marker, the view of the imaging device may be monitored in real-time in order to determine whether the visual marker is within its field of view or if the mobile disinfection apparatus needs to be moved in order to affect such a result. Such monitoring may be performed by a user of a mobile disinfection apparatus or may be done via program instructions of the mobile disinfection apparatus.

As set forth above, the process of positioning a mobile disinfection apparatus denoted in block 50 of FIG. 3 may include positioning a mobile disinfection apparatus in relation to a visual marker which is preselected and/or that is associated with a particular mobile apparatus. It is emphasized that the visual marker may, in some cases, be preselected, but not be associated with the mobile disinfection apparatus and vice versa. In particular, a mobile disinfection apparatus need not have program instructions for detecting or identifying a visual marker in association thereof and the visual marker need not have a means for detecting the mobile apparatus. In such cases, a user of the mobile apparatus or another entity may preselect a visual marker and then the mobile apparatus may be positioned in its vicinity. Alternatively, a visual marker need not be preselected for the positioning step denoted in block 50. In particular, a mobile apparatus may, in some cases, detect a visual marker or be detected by a visual marker upon being in the vicinity of the visual marker, such as during or after a mobile apparatus has been moved in the vicinity of a visual marker. An example of the latter of such cases for the positioning process denoted in block 50 of FIG. 3 may be a mobile disinfection apparatus configured for autonomous movement without intentional positioning to a particular visual marker, wherein the mobile disinfection apparatus detects or identifies a designated visual marker upon passing by or moving to an area in the vicinity of the designated visual marker. In yet other embodiments, the visual marker may be both preselected and associated with the mobile disinfection apparatus.

In some cases, the process of positioning a mobile disinfection apparatus denoted in block 50 of FIG. 3 may include positioning a mobile disinfection apparatus in an area/room such that a visual marker disposed at least approximately 1 foot and, more specifically at least approximately 3 feet, from an entryway (e.g., a door) of an area/room is within a field of view of an imaging device of the mobile disinfection apparatus. As described above, placement of a mobile disinfection apparatus in relation to a visual marker at least approximately 1 foot and, more specifically at least approximately 3 feet from an entryway of the area/room may be advantageous to ensure the mobile disinfection apparatus is fully disposed in the area/room. In addition, placement of a mobile disinfection apparatus in relation to a visual marker at least approximately 1 foot and, more specifically at least approximately 3 feet from an entryway of the area/room may be advantageous to avoid overexposing a space in the area/room in proximity to the entryway and potentially optimize the extent of the area/room which may be sufficiently disinfected (i.e., to achieve at least a 2-log reduction in bacterial contamination on surfaces in the extent of the area/room).

In any case, the flowchart illustrated in FIG. 3 further includes block 52 which denotes receiving notification that the designated visual marker is within the field of view of the imaging device of the mobile disinfection apparatus. In some cases, the notification received in reference to block 52 may be specific for a user of the mobile disinfection apparatus and, thus, the notification may be from an information conveying device of the mobile disinfection apparatus. In such embodiments, the notification may be via any one or more of a visual or audible indicator on the mobile disinfection apparatus, such as but not limited to a lighted bulb, an audible alarm and/or a visual display, the latter of which may include but is not limited to text on a graphical user interface or a video display of the visual marker created by the imaging device of the mobile disinfection apparatus. In other cases, as noted above, the notification may be made via one or more visual or audible indicators on the visual marker. In yet other cases, particularly if the context of block 52 is taken from the perspective of representing program instructions which the mobile apparatuses described herein may include, the notification received in reference to block 52 may additionally or alternatively be a signal sent to a processor of the mobile disinfection apparatus in order for the processor to affect program instructions to analyze the designated visual marker and/or start or conduct operations of the apparatus.

In any case, a record of the mobile disinfection apparatus being positioned such that a visual marker is within the field of view of its imaging device may be made upon receipt of the notification referenced in block 52. The record may be made by a user of the mobile disinfection apparatus and/or the mobile disinfection apparatus may be programmed to do so. In either case, the record may be expressed in a variety of ways, including but not limited to the position of the mobile disinfection apparatus being expressed relative to the visual marker, relative to a particular region or point in an area/room, or relative to a device, object, or structure in an area/room. In general, recording such an event may be beneficial for documenting the mobile disinfection apparatus was placed in a particular position within an area/room relative to a designated visual marker for a disinfection process. Furthermore, automating the mobile disinfection apparatus to do so adds further benefit of eliminating doubt or human error that the apparatus was indeed positioned such the visual marker was within the field of view of the imaging device of the apparatus.

As noted above and described in more detail below, the methods described herein utilize visual marker detection systems to determine, verify, affect and/or convey a variety of information. The methods generally include taking an image of a visual marker and, in some cases, analyzing the image to render the desired information. In reference to the method outlined in FIG. 3, the image of the visual marker may be taken prior or subsequent to receiving the notification referenced in block 52. In embodiments in which the image is taken prior to receiving the notification referenced in block 52, analysis of the image may be conducted prior or subsequent to receiving the notification referenced in block 52. In cases in which an analysis of the visual marker is performed prior to the notification referenced in block 52, the notification may, in some embodiments, be specific to indicating the result/s of the analysis (such as but not limited to whether the mobile disinfection apparatus has been positioned relative to a designated visual marker and/or has been suitably positioned relative to the visual marker). In other cases, result/s of the analysis may be communicated separate from the notification referenced in block 52 or not at all.

It is noted that the steps of taking an image of a visual marker and analyzing the image are not illustrated in FIG. 3 since the blocks outlined in the flowchart of FIG. 3 may represent processes performed by a user of the mobile disinfection apparatus. Conversely, the step of taking an image of a visual marker is performed by the imaging device of the mobile disinfection apparatus and the step of analyzing the image is performed by the imaging device and/or program instructions of the mobile disinfection apparatus. As noted above, the blocks outlined in the flowchart of FIG. 3 may alternatively represent program instructions of the mobile apparatus (including that of its imaging device) and, thus, in such a context the steps of taking an image of a visual marker and analyzing the image may be presumed as part of FIG. 3. Examples of possible scenarios in which an image of a visual marker may be taken and optionally analyzed, to which the methods disclosed herein are particularly directed, include those described in reference to FIGS. 6-11 below.

In any case, an imaging device of a mobile apparatus may be activated to take an image of a visual marker in response to various incidents. For example, an imaging device may, in some embodiments, be automatically activated to take an image upon the mobile apparatus detecting a visual marker. In other cases, an imaging device may be automatically activated to take an image upon the mobile apparatus detecting and/or receiving a signal that the mobile apparatus has been suitably positioned relative to a visual marker (a process of which is described in more detail below in reference to FIG. 7). Alternatively, the imaging device may be activated by a user of the mobile disinfection apparatus, particularly by the user activating an input control on the mobile disinfection apparatus. The input control may include but is not limited to a button on the mobile disinfection apparatus, a selection on a touch screen on the mobile disinfection apparatus, or a mechanism to lock the position of the mobile disinfection apparatus in an area/room. Regarding the latter of such options, the mobile disinfection apparatus may include circuitry coupled between the mechanism and the imaging device such that upon activation of the mechanism the imaging device is activated to take an image.

In yet other embodiments, the imaging device may be automatically activated to take an image subsequent to detecting the mobile disinfection apparatus coming to a stop. In particular, the mobile disinfection apparatus may, in some embodiments, include a sensor to detect its own motion, such as but not limited to a speedometer, an accelerometer and/or a gyroscope, and further include program instructions to affect activation of the imaging device to take an image subsequent to detecting the apparatus coming to a stop. Such functionality may be advantageous for cases in which a user is manipulating the position of a mobile disinfection apparatus relative to a visual marker or when the mobile disinfection apparatus has received instruction to move to a particular location in an area/room having a visual marker. A flowchart of the program instructions is illustrated in FIG. 4. In particular, the flowchart in FIG. 4 includes block 70 for monitoring the motion of the mobile disinfection apparatus, block 72 for detecting when the mobile apparatus comes to a stop, and block 74 for sending a signal to the imaging device of the apparatus to obtain an image. It is noted that the process denoted in block 74 may be conducted any time subsequent to detecting the apparatus coming to a stop, including immediately thereafter or after a predetermined duration thereafter, but in either case the imaging device is activated while the mobile apparatus is stopped. As set for the above, the process denoted in FIG. 4 as well as the processes denoted in FIGS. 3 and 5-12 may be used for any type of mobile apparatus, not just mobile disinfection apparatuses.

Turning back to FIG. 3, the flowchart illustrated therein further includes block 54 which denotes activating the positioned mobile disinfection apparatus to start and conduct a disinfection process in the area/room. In some cases, the activation of the positioned mobile disinfection apparatus recited in block 54 may be performed by a user of the mobile disinfection apparatus, particularly via a user interface that is in electrical communication with the mobile disinfection apparatus (e.g., via integrated user interface 20 or detached user interface 22 described in reference to FIG. 2). In yet other cases, the activation of the positioned mobile disinfection apparatus to start and conduct a disinfection process may be conducted by a controller of the mobile disinfection apparatus, specifically via program instructions in response to one or more signals received at the controller to do so. Examples of program instructions for such a purpose may include but are not limited to those described in more detail below in reference to FIGS. 5-9, 11 and 12.

In any case, activation of a mobile disinfection apparatus to start and conduct a disinfection process does not necessarily mean a germicidal source of the apparatus is automatically activated at the same time or immediately thereafter and, in some cases, further notification may be necessary to activate a germicidal source of an apparatus for a disinfection process. For instance, in some cases, a mobile disinfection apparatus may include program instructions to activate a germicidal source of the apparatus to generate and project a germicide at a predetermined time after receiving notice that the mobile disinfection apparatus has been activated to start and conduct a disinfection process. Alternatively, a mobile disinfection apparatus may, in some cases, include program instructions to activate a germicidal source of the apparatus to generate and project a germicide after receiving notice that one or more process steps and/or provisions have been completed. More specifically, a mobile disinfection apparatus may, in some cases, include program instructions to activate its germicidal source after receiving notice that the apparatus has been activated to start and conduct a disinfection process and after receiving a subsequent notice that one or more process steps and/or provisions have been completed. In this manner, it may be ensured that the one or more process steps and/or provisions are conducted prior to the germicidal source being activated to generate and project a germicide. In other cases, one or more process steps and/or provisions may be conducted prior to activating a positioned mobile disinfection apparatus to start and conduct a disinfection process.

In fact, the timing to conduct process steps and/or provisions which are to be performed prior to activation of a germicidal source for a disinfection process may be any time prior to, during and/or subsequent to the process of positioning the mobile disinfection apparatus referenced in block 50. FIG. 3 denotes such a variety of options by dotted lines 60, 62 and 63. In particular, dotted line 60 denotes that any process steps and/or provisions, including but not limited to the processes described in reference to blocks 64, 66 and 68, may be conducted prior to the positioning process described in reference to block 50. In addition, dotted lines 62 and 63 respectively denote any process steps and/or provisions, including but not limited to the processes described in reference to blocks 64, 66 and 68, may be conducted prior or subsequent to the process of activating the positioned mobile disinfection apparatus to start and conduct a disinfection process as described in reference to block 54. It is noted that dotted lines 62 and 63 are double-arrowed lines, indicating any process steps and/or provisions such as but not limited to the processes described in reference to blocks 64, 66 and 68 may be performed prior to or subsequent to the process described in reference to 54 and then return to such a point in the flowchart thereafter. Furthermore, it is noted that not all of the process steps and/or provisions need to be performed at the same time or even all prior to or subsequent to block 50 or 54. In particular, any number of process steps and/or provisions may be performed at any of the timings denoted by dotted lines 60, 62 and 63. In general, the dotted lines in FIG. 3 indicate possible variations of the order of process steps or the point at which to integrate process steps into the illustrated flowchart.

In any case, process steps and/or provisions which may be performed prior to activation of a germicidal source for a disinfection process may include a variety of actions, depending on the configuration of the mobile disinfection apparatus and/or the area/room in which the disinfection process is to be conducted. For instance, in some cases, the process steps and/or provisions may include a checklist of tasks to prepare the mobile disinfection apparatus and/or the area/room in which the apparatus is arranged for the ensuing disinfection process. In addition or alternatively, the process steps and/or provisions may include one or more safety precautions to ensure operation of the mobile disinfection apparatus does not harm individuals, i.e., if the operation of the mobile disinfection apparatus requires such. In particular, a mobile disinfection apparatus may, in some cases, be configured to project a germicide that is hazardous to human health into its ambient and, thus, safety precautions may need to be taken to ensure individuals are not exposed to it during a disinfection process. For example, the process steps and/or provisions may, in some cases, include one or more safety precautions to ensure the area/room in which the mobile disinfection apparatus is arranged is unoccupied prior to activation of its germicidal source. In other cases, one or more safety precautions may include insuring shields are in place to protect occupants of an area/room from being exposed to a hazardous germicide. In such cases, the shields may be attached to the mobile disinfection apparatus and/or may be separate from the apparatus. In any case, examples of germicides which are considered hazardous to human health include but are not limited to ultraviolet light and corrosive chemicals in the form of a liquid, gas or mist.

An example of a safety precaution to ensure an area/room is unoccupied prior to a disinfection process being conducted includes but is not limited to a predetermined delay after the mobile disinfection apparatus has been activated to start and conduct a disinfection process to allow individuals to leave the area/room. In addition or alternatively, one or more occupancy sensors of a mobile disinfection apparatus may be activated prior to activating its germicidal source to determine whether the area/room is occupied. More details regarding such precautions as well as examples of other tasks and/or safety precautions that may be performed before a germicidal source of a mobile disinfection apparatus is activated for a disinfection process are described in reference to blocks 64, 66 and 68 of FIG. 3 as well as in reference to block 76 of FIG. 5. It is noted, however, that additional and/or alternative tasks may be performed to prepare a mobile disinfection apparatus and/or an area/room for a disinfection process and/or to ensure an area/room is unoccupied for a disinfection process.

In any case, process steps and/or provisions to be conducted prior to the activation of a germicidal source of a mobile disinfection apparatus may, in some cases, be performed by a user of the apparatus. In addition or alternatively, the mobile disinfection apparatus may be configured to perform the process steps and/or provisions (i.e., the mobile disinfection apparatus may be configured with means to affect the process steps and/or provisions and may further include program instructions to activate such means). In any case, the process steps and/or provisions need not be conducted at the same time or in immediate succession of each other. Furthermore, notice that the process steps and/or provisions have been completed may be activated by a user of the mobile disinfection apparatus and/or the mobile disinfection apparatus may include program instructions to activate such notices.

As shown in block 64 of FIG. 3, a power plug of a mobile disinfection apparatus may be plugged into a power socket of an area/room to prepare for a disinfection process to be performed in the area/room. In some configurations, however, a mobile disinfection apparatus may include a battery as a power source for a disinfection process and, thus, block 64 may, in some cases, be omitted from the method outlined in FIG. 3. As shown in block 66 of FIG. 3, one or more entryways to an area/room may, in some cases, be secured prior to a disinfection process being performed therein such that access to the area/room is deterred during the disinfection process. Such a process may include but is not limited to placing warnings signs on and/or in the vicinity of the exterior of the entryway/s such that persons are deterred from entering the area/room. In addition or alternatively, the process may include blocking or locking entryway/s. In some cases, a door movement sensor may be placed on, in the vicinity and/or in alignment with an entryway (i.e., on either the interior or exterior side of the entryway) to prepare for a disinfection process to be performed in an area/room. In such cases, the door movement sensor may be communicably coupled to the mobile disinfection apparatus to send a signal when a closed door to the entryway moves during a disinfection process. In addition, the mobile disinfection apparatus may include program instructions to deactivate its germicidal source upon receiving the signal from the door movement sensor. In other cases, entryway/s of an area/room need not be secured prior to a disinfection process being performed therein and, thus, block 66 may, in some embodiments, be omitted from the method outlined in FIG. 3.

In some cases, an area/room may be vacated of all people and animals prior to a disinfection process being performed therein as shown in block 68 of FIG. 3. In some cases, the process referenced in block 68 may be performed by a person, particularly by the person scanning the room prior to vacating the room themselves. In some cases, prior to vacating the room themselves, the person may check a room that is interior to the area/room (e.g., a bathroom of a patient room) to make sure it is void of people and animals that could potentially enter the area/room during the subsequent disinfection process. In addition or alternatively, a person could activate an occupancy sensor in the area/room and then vacate the room. In yet other cases, the mobile disinfection apparatus may be programmed to automatically activate the occupancy sensor as described in more detail below in reference to FIG. 5. In any of such cases, the mobile disinfection apparatus is coupled to the occupancy sensor and includes program instructions to inhibit or terminate activation of the germicidal source upon the occupancy sensor detecting occupancy. In some cases, however, an area/room need not be vacant for the mobile disinfection apparatus to perform a disinfection process and, thus, an area/room may not need to be vacated prior thereto. As such, block 68 may, in some embodiments, be omitted from the method shown and described in reference to FIG. 3. In some such cases, shields may be positioned in an area/room to protect occupants of the area/room from being exposed to a hazardous germicide during a subsequent operation of mobile disinfection apparatus. In yet other cases, individuals may not need to be protected from an operation of a disinfection apparatus and, thus, the process of positioning such shields may be foregone.

An example set program instructions which a mobile disinfection apparatus may include regarding the activation of an occupancy sensor and its effect on the operation of a germicidal source of the mobile disinfection apparatus is illustrated in FIG. 5. In particular, the flowchart shown in FIG. 5 includes block 76 for activating an occupancy sensor of a mobile disinfection apparatus. The activation of the occupancy sensor may, in some cases, be in response to an activated input control on the occupancy sensor itself. Alternatively, the activation of the occupancy sensor may be in response to an activated input control on a user interface of the disinfection apparatus that is specifically designated for activating the occupancy sensor. In yet other cases, the activation of the occupancy sensor may be in response to an activated input control on a user interface of the disinfection apparatus that is designated to activate the disinfection apparatus to start and conduct a disinfection process. In other cases, an occupancy sensor may be activated in response to activities of other components of the mobile apparatus, such as but not limited to its imaging device. In any case, the occupancy sensor and/or the controller of the mobile apparatus may be configured to activate the occupancy sensor any time subsequent to receiving signals to do so, including immediately thereafter or after a predetermined duration thereafter.

As further shown in FIG. 5 via block 78, a mobile disinfection apparatus may include program instructions for activating a germicidal source of the disinfection apparatus upon the occupancy sensor not detecting occupancy for a predetermined amount of time in the area/room in which the mobile disinfection apparatus is arranged. The predetermined amount of time may vary for different applications. An example range of a predetermined amount of time for not detecting occupancy may be between approximately 30 seconds and approximately 3 minutes, but shorter or longer time frames may be considered. In any case, as shown by block 79 in FIG. 5, the mobile disinfection apparatus may include program instructions for inhibiting or terminating activation of the germicidal source upon the occupancy sensor detecting occupancy. More specifically, the mobile disinfection apparatus may include program instructions for inhibiting activation of the germicidal source upon the occupancy sensor detecting occupancy prior to activation of the germicidal source in block 78. In addition, the mobile disinfection apparatus may include program instructions for terminating activation of the germicidal source upon the occupancy sensor detecting occupancy subsequent to activation of the germicidal source in block 78. For both cases, the mobile disinfection apparatus may include program instructions to send a notification to a detached user interface of the disinfection apparatus to convey that the activation of the germicidal source has been inhibited or terminated. In some cases, the germicidal source of the mobile disinfection apparatus may be reactivated upon the occupancy sensor not detecting occupancy for a predetermined amount of time subsequent to the activation of the germicidal source being inhibited or terminated in block 79.

Regardless of whether a mobile disinfection apparatus is used in conjunction with an occupancy sensor, a mobile disinfection apparatus may include program instructions to terminate its germicidal source upon receipt of a signal from a user interface of the apparatus and/or upon completion of a disinfection process. In particular, a mobile disinfection apparatus may include program instructions to terminate its germicidal source upon receipt of a signal from a user interface (integrated and/or detached from the apparatus) indicating an input control thereof has been activated to terminate operation of the germicidal source. In addition or alternatively, a mobile disinfection apparatus may include program instructions to terminate its germicidal source upon receipt of a signal indicating a disinfection process is complete.

A signal indicating a disinfection process is complete may be from a timer in the apparatus, navigational sensors of the apparatus or a germicidal dose sensor communicably coupled to the apparatus. In particular, a disinfection process may, in some cases, be conducted for a preset duration and, thus, a mobile disinfection apparatus may, in some cases, include a timer which is started upon the germicidal source of the apparatus being activated. The mobile disinfection apparatus is further configured to send a signal at the end of the preset duration to terminate operation of the germicidal source. In addition or alternatively, in scenarios in which a mobile disinfection apparatus is programmed to follow a predetermined path during a disinfection process, navigational sensors of the mobile apparatus may send a signal at the end of route to indicate the completion of the disinfection process. In yet other cases, a germicidal dose sensor may be communicably coupled to a mobile disinfection apparatus and the dose sensor may send a signal to terminate operation of the germicidal source of the apparatus upon determining a predetermined level of germicide has been received. In such cases, the germicidal dose sensor may be integrated in the mobile disinfection apparatus or may be disposed in the area/room in which the apparatus is arranged but detached therefrom.

It is noted that a mobile apparatus having program instructions to terminate operation of a germicidal source upon receipt of a signal from a timer is not mutually exclusive to the mobile disinfection apparatus having program instructions to terminate operation of a germicidal source upon receipt of a signal from a germicidal dose sensor communicably coupled thereto. In particular, a mobile disinfection apparatus may include program instructions for both and, thus, may be configured to terminate operation of its germicidal source upon receipt of a signal from either a timer or a germicidal dose sensor. More specifically, a mobile disinfection apparatus may include program instructions for terminating operation of its germicidal source after a predetermined duration unless a predetermined level of germicide is detected prior to such.

Turning back to FIG. 3 and as shown in block 56, the method outlined in FIG. 3 may, in some cases, include repositioning the mobile disinfection apparatus such that a different designated visual marker is within the field of view of the imaging device of the mobile disinfection apparatus.

In some cases, the mobile disinfection apparatus may be repositioned subsequent to an operation of a germicidal source of the apparatus being terminated and/or subsequent to the apparatus receiving a signal that the disinfection process referenced in block 54 is complete. In this manner, the mobile disinfection apparatus may be repositioned while the germicidal source is deactivated, which may be done manually, via user input controls or autonomously. It is noted that in such a scenario the disinfection process conducted in reference to block 54 may be conducted at a fixed location (i.e., the location associated with the designated visual marker detected in reference to block 50) or can include the apparatus moving during the process and ending up at the same or different spot from where the disinfection process started.

In yet other cases, the method of repositioning the mobile disinfection apparatus in reference to block 56 in FIG. 3 may be conducted while the germicidal source of the apparatus is generating and emitting a germicide. Although in such cases a mobile disinfection apparatus may be repositioned generally any time during a disinfection process, a mobile disinfection apparatus may, in some cases, be repositioned specifically after a particular operational set point of the disinfection process has been met. For example, a mobile disinfection apparatus may, in some cases, be repositioned specifically after a lapse of a predetermined amount of time and/or after an accumulated germicidal dose has been measured at a particular location. In particular, for some disinfection processes, a mobile disinfection apparatus may be moved and stopped at multiple locations in an area/room or among multiple areas/rooms (i.e., while the germicidal source is operating to generate and emit a germicide) to focus the disinfection process at each of the multiple locations. In some of such cases, a mobile disinfection process may be programmed to conduct the disinfection process for a particular amount of time at each location (i.e., the same amount of time or a different amount of time among the locations) and, thus, in some cases, a mobile disinfection apparatus may, in some cases, be repositioned specifically after a lapse of a predetermined amount of time. In addition or alternatively, a mobile disinfection process may be programmed to conduct the disinfection process until a particular amount of germicidal dose is measured at each location and, thus, a mobile disinfection apparatus may, in some cases, be repositioned specifically after an accumulated germicidal dose has been measured.

In some cases, the different designated visual marker referenced in block 56 may be disposed in a different defined area/room than the defined area/room referenced in block 50. In other words, the process referenced in block 56 may refer to moving the mobile disinfection apparatus to a different area/room. In yet other cases, the different designated visual marker referenced in block 56 may be disposed in same the defined area/room as referenced in block 50. In other words, the process referenced in block 56 may refer to moving the mobile disinfection apparatus to a different location within the area/room in which it is arranged such that a different designated visual marker in the area/room is within the field of view of the imaging device of the mobile disinfection apparatus.

The latter of such scenarios may be particularly suitable for relatively large areas/rooms, such as areas/rooms having a footprint greater than approximately 100 $ft^2$. In particular, operating a mobile disinfection apparatus at multiple positions in relatively large areas/rooms may be desirable such that a particular germicidal efficacy may be attained throughout the area/room (i.e., depending on the distance the mobile disinfection apparatus is configured to distribute an effective amount germicide). In addition or alternatively, regardless of the size of an area/room, it may be advantageous to operate a mobile disinfection apparatus at multiple positions in an area/room to disinfect different sides of objects in the area/room. For example, it may be desirable to operate a mobile disinfection apparatus on opposing sides of a patient bed or opposing sides of machinery or equipment in a pharmaceutical laboratory (such as but not limited to inspection tables, vats, filling stations, etc.). It is noted that similar advantages may be realized for other types of mobile apparatuses (i.e., mobile apparatuses which are not disinfection apparatuses) if the operations of the mobile apparatuses affect or are affected by the ambient in which they are arranged. Thus, as noted above, the method set forth in FIG. 3 may be applicable to mobile apparatuses other than mobile disinfection apparatuses.

In some cases, a mobile disinfection apparatus may include program instructions to inform a user of the apparatus to move it to a different location (i.e., to a location in a different area/room or to a different location in the same area/room referenced in block 50). The notification may be sent via any one or more of a visual or audible indicator on the mobile disinfection apparatus (including a detached user interface thereof). In some cases, the notification sent may communicate a specific location and/or a specific visual marker for the user to move the apparatus to. Alternatively, the notification may simply state to move the apparatus for a subsequent disinfection process. In the latter of such scenarios, the user may be trained to know an appropriate location and/or a visual marker to move the apparatus to, although the methods described herein are not necessarily so limited to such. In yet other cases, a mobile disinfection apparatus may be configured and programmed to automatically move itself to a particular location. In any case, the movement of the mobile disinfection apparatus is such that a different visual marker is within a field of view of an imaging device of the apparatus and the action/s of a user or the mobile disinfection apparatus to induce such movement may generally include those described above for block 50 of FIG. 3.

In some cases, as noted by dotted line 58 in FIG. 3 between blocks 56 and 52, notification may be received that the different designated visual marker is within the field of view of the imaging device of the mobile disinfection apparatus. In yet other cases, such a notification may not be received and, thus, the dotted line extending from block 56 may be omitted. Alternatively, in cases in which a mobile disinfection apparatus is moved after completion of a disinfection process, the mobile disinfection apparatus may be reactivated to start and conduct another disinfection process and, thus, the dotted line extending from block 56 may be alternatively routed to block 54. In any case, the protocols and options regarding the positioning process, notification process and activating process respectively described above in reference to blocks 50, 52 and 54 may dually apply to the repositioning the mobile disinfection apparatus described in reference to block 56 as well as the possible notification and reactivation processes conducted subsequent to repositioning the mobile disinfection apparatus. In addition, in cases in which a mobile disinfection apparatus is moved after completion of a disinfection process, one or more other process steps and/or provisions (such as but not limited to the tasks and/or safety precautions discussed in reference to blocks 64, 66, and 68 of FIG. 3 or block 76 of FIG. 5) may be conducted subsequent to repositioning the mobile disinfection apparatus but prior to reactivating the mobile disinfection apparatus to start and conduct another disinfection process in the area/room.

In some cases, a mobile disinfection apparatus may include program instructions to determine whether a location to which the apparatus is repositioned is different from a previous location at which the apparatus was arranged. More specifically, a mobile disinfection apparatus may include program instructions to determine whether a visual marker in view of an imaging device of the mobile disinfection apparatus is different from a visual marker that was used to previously determine or verify a position a mobile disinfection apparatus. An exemplary compilation of program instructions for such a determination is set forth in more detail below in reference to FIG. 6. In particular, and as shown in block 80 of FIG. 6, a mobile disinfection apparatus may include program instructions for analyzing an image obtained by an imaging device of the apparatus. As noted above, such a process may take many forms, including but not limited to comparing the image to a database of images, comparing the image to one or more previous images taken by the imaging device, analyzing the size, shape, contour, clarity and/or placement of a visually identifiable mark in the image, and/or decoding the image.

In any case, in the context of a scenario in which a user moves a mobile disinfection apparatus or a mobile disinfection apparatus moves itself from a location of a first visual marker (e.g., a location at which a disinfection cycle was previously conducted by the apparatus) to a different visual marker, the process of block 80 may refer to analyzing a different image obtained by the imaging device. For such cases, as denoted by block 82 in FIG. 6, a mobile disinfection apparatus may include program instructions for determining whether the visual marker in the image is different from a visual marker of an image previously obtained by the imaging device of the apparatus. In some cases, the process denoted in block 82 may be specific to determining whether the visual marker is different from a visual marker of a most recent image obtained by the imaging device of the apparatus (i.e., the most recent image being the image obtained by the imaging device most previous to the newly obtained image being analyzed in reference to block 80). In any case, it is noted that one skilled in the art would be apprised that the process denoted in block 82 could be altered to determine whether the images are the same and, consequently, the execution of the particular actions based thereon could be reversed from the depiction in FIG. 6.

Figure 6:
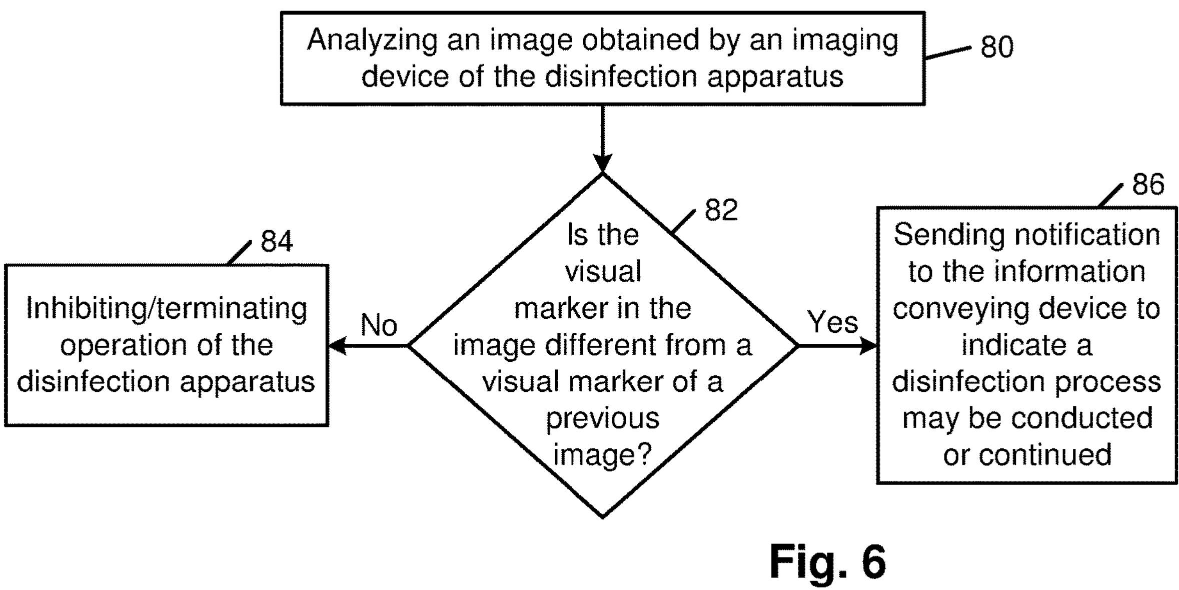

In any case, the process denoted in block 82 of FIG. 6 may involve comparing one or more features of the two visual markers, comparing designations assigned to the two visual markers, and/or comparing information decoded from the two visual markers. In particular, images obtained by an imaging device of a mobile disinfection apparatus and/or information regarding visual markers in the images may, in some cases, be saved in a memory of the apparatus or to a database that is accessible by the apparatus. As such, a mobile disinfection apparatus may include program instructions to compare one or more features of a visual marker in a newly obtained image (or the visual marker as a whole) to that of a visual marker of a previous image to determine whether the visual markers in the images are the same of different. In addition or alternative cases, images obtained by an imaging device of a mobile disinfection apparatus may be assigned descriptors specific to the visual markers which the images contain and those descriptors may be saved in a memory of the apparatus or to a database that is accessible by the apparatus. In this manner, the descriptors of different images may be compared to determine if the visual markers in the images are the same or different. In yet other cases, visual markers in images obtained by an imaging device of a mobile disinfection apparatus may be decoded and the information obtained therefrom can be compared to information decoded from a visual marker of a previous image that is saved in a memory of the apparatus or in a database that is accessible by the apparatus. In this manner, the decoded information of the visual markers may be compared to determine if they are the same or different.

In any case, a mobile disinfection device may be programmed to save any information (e.g., the images themselves, descriptors of visual markers, and/or decoded information) pertaining to images its imaging device has obtained. In some cases, a mobile disinfection device may be programmed to automatically delete the oldest information upon some threshold being met, such as after a set amount of time, after the mobile disinfection device has performed a set number of disinfection cycles and/or after the imaging device has obtained a set number of images. In this manner, the amount of information stored for images may be controlled. Regardless of the amount of information stored or the manner in which the determination in block 82 is made, a mobile disinfection apparatus may include program instructions for conducting particular actions based on whether the visual marker in the most recent image is the same or is different than a visual marker to which it is compared. In particular, as denoted in block 84 of FIG. 6, a mobile disinfection apparatus may include program instructions for inhibiting or terminating operation of its germicidal source and possibly other components of the apparatus to conduct a disinfection process if the visual marker in the most recent image is the same as a visual marker to which it is compared in reference to block 82. In addition or alternatively, a mobile apparatus may include program instructions for sending notification to an information conveying device of the apparatus to indicate the apparatus has not been properly positioned if the visual marker in the most recent image is the same as a visual marker to which it is compared in reference to block 82.

Likewise and as denoted in block 86 of FIG. 6, a mobile disinfection apparatus may, in some cases, include program instructions for sending notification to an information conveying device of the apparatus to indicate a disinfection process may be conducted or continued if the visual marker in the most recent image is different than a visual marker to which it is compared in reference to block 82. In some cases, however, such a notification may not be sent and, thus, block 86 may be omitted form FIG. 6. As noted above in reference to block 56 of FIG. 3, a mobile disinfection apparatus may include program instructions to automatically activate the apparatus to start and conduct a disinfection process after being repositioned such that a different designated visual marker is within the field of view of the imaging device of the apparatus. As such, in reference to FIG. 6, a mobile disinfection apparatus may, in some cases, include program instructions for automatically activating the apparatus to start and conduct a new disinfection process upon determining the visual marker in the most recent image is different than a visual marker to which it is compared in reference to block 82. In some cases, one or more process steps and/or provisions, such as but not limited to the processes described above for blocks 64-68 of FIG. 3 or block 76 of FIG. 5, may be conducted by a user or the mobile disinfection apparatus subsequent to the notification referenced in block 86 being sent (if applicable), but prior to activating the mobile disinfection apparatus to start and conduct the new disinfection process. In any case, the mobile disinfection apparatus may, in some cases, include program instructions to record that the apparatus has been positioned such that a different visual marker is in a field of view of an imaging device of the apparatus upon determining the visual marker in the most recent image is different than a visual marker to which it is compared in reference to block 82.

As set forth above, the mobile apparatuses and methods provided herein may be configured to utilize visual marker detection systems to determine and/or verify a mobile apparatus has been suitably positioned at a preset location in an area/room or at a location a preset distance from a structure in an area/room. An exemplary compilation of program instructions directed to such an objective is set forth in FIG. 7. In general, the process outlined in FIG. 7 may be employed or integrated with any of the processes described herein, examples of which include but are not limited to being between the processes described in reference to blocks 52 and 54 of FIG. 3, subsequent to a confirmation that a visual marker is different from a visual marker of a previous image obtained by an image detection device of a mobile apparatus as described in reference to block 82 of FIG. 6, between the processes described in reference to blocks 106 (or block 122) and 108 of FIG. 8, prior to the processes described in reference to blocks 130 and 150 of respective FIGS. 9 and 10, between the processes described in reference to blocks 160 and 162 of FIG. 11, and between the processes described in reference to blocks 170 and 172 of FIG. 12.

Figure 7:
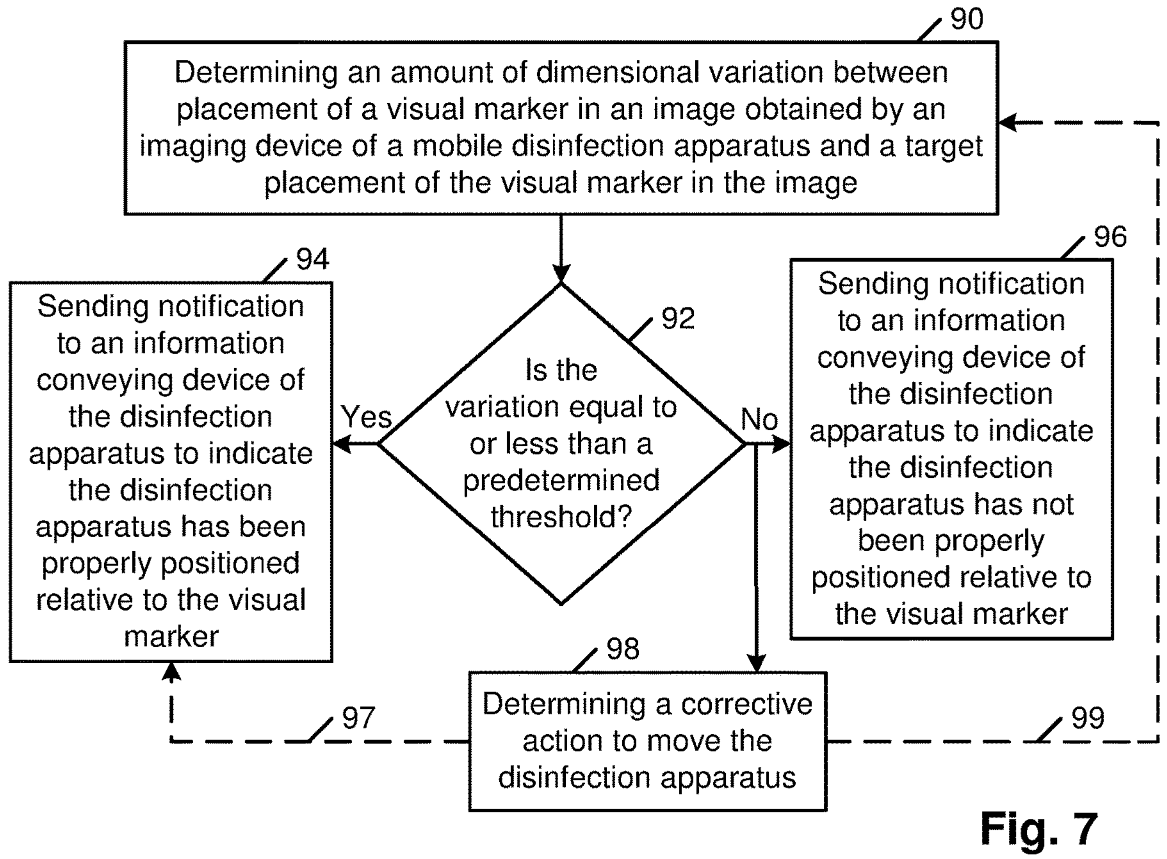

FIG. 7 shows a flowchart including block 90 in which an amount of dimensional variation between an actual placement of a visual marker in an obtained image and a target placement of the visual marker in the image is determined. Such a process may be conducted automatically upon the imaging device detecting the visual marker or may be conducted upon receipt of a signal from an input control on a user interface communicably coupled to the apparatus. More specifically, in the latter of such cases, a user interface communicably coupled to the apparatus may include an input control to allow a user of the apparatus to select when and if the process of block 90 is to be conducted. In some cases, a mobile disinfection apparatus may be programmed to inhibit activation of its germicidal source unless the process of block 90 is conducted and, in some cases, until the determined dimensional variation is equal to or less than a predetermined threshold (a process of which is discussed in more detail below in reference to block 92 of FIG. 7). In other cases, however, the process of block 90 need not be required prior to a disinfection process being performed by a mobile disinfection apparatus. In this manner, the selection to induce such a process by an input control on a user interface may be optional.

In any case, the target placement of a visual marker in an image may vary depending on the specifications of the visual marker detection system and/or the disinfection process to be performed at a location in an area/room associated with the visual marker. In some cases, the target placement of a visual marker in an image may be a central position in the image, but variances to centralizing a target placement of a visual marker in an image may also be considered. For example, if a visual marker is located at a position which would place a mobile apparatus centrally aligned therewith in too close of proximity to a structure in the area/room for a disinfection process, it may be advantageous to have the target placement of the visual marker off-center in an image.

As shown in block 92 of FIG. 7, a mobile disinfection apparatus may include program instructions to determine whether the variation determined in block 90 is equal to or less than a predetermined threshold. More specifically, a mobile disinfection apparatus may include program instructions to compare the variation determined in block 90 to a predetermined threshold and, then execute particular actions depending on whether the variation is less than, equal to, or greater than the predetermined threshold. In general, the predetermined threshold may vary among applications, particularly depending on the preciseness needed to verify an apparatus is suitably positioned at a particular location in an area/room. An example range for a predetermined threshold for a mobile disinfection apparatus may be between approximately 1 inch and approximately 24 inches, but smaller or larger thresholds may be considered. In any case, it is noted that one skilled in the art would be apprised that the process denoted in block 92 of determining whether the dimensional variation is equal to or less than a predetermined threshold could be altered to determine whether the dimensional variation is equal to or greater than a predetermined threshold and the execution of the particular actions based thereon may be reversed from the depiction in FIG. 7. Furthermore, it is noted that one skilled in the art would be apprised that the inclusion of 'equal to' in either scenario may be dropped.

As shown in block 94 of FIG. 7, a mobile disinfection apparatus may, in some cases, include program instructions for sending notification to an information conveying device communicably coupled to the apparatus to indicate the disinfection apparatus has been properly positioned relative to the visual marker subsequent to determining the amount of dimensional variation is equal to or less than the predetermined threshold. In addition or alternatively, a mobile apparatus may include program instructions for automatically activating the apparatus to start and conduct a disinfection process upon determining the amount of dimensional variation is equal to or less than the predetermined threshold. Furthermore, the mobile disinfection apparatus may, in some cases, include program instructions to record that the apparatus has been properly positioned relative to the visual marker upon determining the amount of dimensional variation is equal to or less than the predetermined threshold.

Likewise and as denoted in block 96 of FIG. 7, a mobile disinfection apparatus may, in some cases, include program instructions for sending notification to an information conveying device communicably coupled to the apparatus to indicate the disinfection apparatus has not been properly positioned relative to the visual marker subsequent to determining the amount of dimensional variation is greater than the predetermined threshold. In addition or alternatively, a mobile apparatus may include program instructions for inhibiting or terminating activation of its germicidal source and possibly other components of the apparatus to conduct a disinfection process if the amount of dimensional variation is greater than the predetermined threshold. Furthermore, the mobile disinfection apparatus may, in some cases, include program instructions to record that the apparatus has not been properly positioned relative to the visual marker upon determining the amount of dimensional variation is greater than the predetermined threshold.

In some cases, a mobile disinfection apparatus may include program instructions for determining a corrective action for moving the disinfection apparatus when the amount of dimensional variation is greater than the predetermined threshold as shown in block 98 of FIG. 7. For example, a mobile disinfection apparatus may include program instructions for determining one or more directions the apparatus needs to move and what distance in each direction to more suitably position the apparatus at a desired location.

In some cases, the corrective action may include directions sufficient to move the apparatus to the desired location. In other cases, however, such precision may not be needed and, thus, the corrective action may include directions sufficient to move the apparatus such that the amount of dimensional variation between a placement of the visual marker in a second image subsequently obtained by the imaging device and a target placement of the visual marker in the second image is equal to or less than the predetermined threshold.

In some cases, the corrective action determined in reference to block 98 may be included in the notification sent in reference to block 96. In other cases, the corrective action may be sent in a different notification or in a different manner to an information conveying device of the apparatus. In any of such cases, the corrective action sent to an information conveying device may enable a user to move (either manually or via user input control) the mobile disinfection apparatus in the manner indicated and the corrective action may be visual or audible. For example, in some cases, the corrective action may be text and/or symbols on a graphical user interface of the mobile disinfection apparatus (i.e., on its main unit and/or on detached user interface) indicating the direction and distance to move the apparatus. In addition or alternatively, a mobile disinfection apparatus may include a visual display for displaying what the imaging device is currently viewing (i.e., a video display of the view or a computer-generated representation of the view) and the corrective action may include indicia on the visual display for moving the apparatus to a more desired location. For example, the visual display may include one or more lines to represent the periphery of the mobile disinfection apparatus and one or more other lines to represent a desired location for the mobile disinfection apparatus. In such cases, visual display may include instructions to overlap the lines representing the mobile disinfection apparatus and the desired location or a user of the apparatus may be trained to do so without instructions on the visual display. In addition or alternatively, the instructions to overlap the lines may be audible. It is noted that other indicia (i.e., other than lines) may be used on the visual display to aid a user in moving a mobile disinfection apparatus to a more desired location.

In yet other embodiments, a mobile disinfection apparatus may be configured to automatically move itself prescribed distance/s in one or more directions in accordance with a corrective action determined at block 98. In particular, a mobile disinfection apparatus may include wheels, a motor to automate movement of the wheels, and program instructions to actuate the motor in accordance with the instructions of the corrective action. Regardless of the manner in which a corrective action determined at block 98 is implemented, a mobile disinfection apparatus may, in some cases, include program instructions to record that the corrective action has been implemented. In some cases, the mobile disinfection apparatus may include program instructions to send notification to an information conveying device of the apparatus subsequent to the corrective action being implemented to indicate the disinfection apparatus has been properly positioned relative to the visual marker, such as shown in FIG. 7 by dotted line 97 between blocks 98 and 94. Alternatively, the mobile disinfection apparatus may, in some cases, include program instructions to obtain a new image of the visual marker and then determine an amount of dimensional variation between a placement of the visual marker in the newly obtained image and a target placement of the visual marker in the newly obtained image, such as indicated in FIG. 7 by dotted line 99 between blocks 98 and 90. In yet other cases, the mobile disinfection apparatus may not include either of such program instructions. In general, the dotted lines illustrated in FIG. 7 indicate possible variations at to the course of action which may be performed subsequent to the process described in reference to block 98.

As set forth above, the mobile apparatuses and methods provided herein may be configured to utilize visual marker detection systems to determine whether a visual marker is associated with a mobile disinfection apparatus. In particular, it is contemplated that an area/room, or multiple areas/rooms or an entire facility may include multiple visual markers and, in some cases, less than all of such multiple visual markers may be associated with a mobile disinfection apparatus for the placement and/or operation of the apparatus in the area/room. As such, it may be advantageous to definitively position a mobile disinfection apparatus relative to a visual marker that is associated with the mobile disinfection apparatus. In addition, the mobile apparatuses and methods provided herein may be configured to utilize visual marker detection systems to affect the operation of a mobile apparatus, particularly to control when and/or what manner the mobile apparatus may be operated. An exemplary compilation of program instructions directed to such objectives is set forth in FIG. 8. One or more of the process steps outlined in FIG. 8 (including all and less than all) may be employed or integrated with any of the other processes described herein, examples of which include but are not limited to being prior to the processes described in reference to block 54 in FIG. 3, subsequent to the processes described in reference to block 86 in FIG. 6, prior to the processes described in reference to blocks 90 and 130 of respective FIGS. 7 and 9, prior or subsequent to the process described in reference to block 150 of FIG. 10, and prior to the processes described in reference to blocks 162 and 172 of respective FIGS. 11 and 12.

Figure 8:
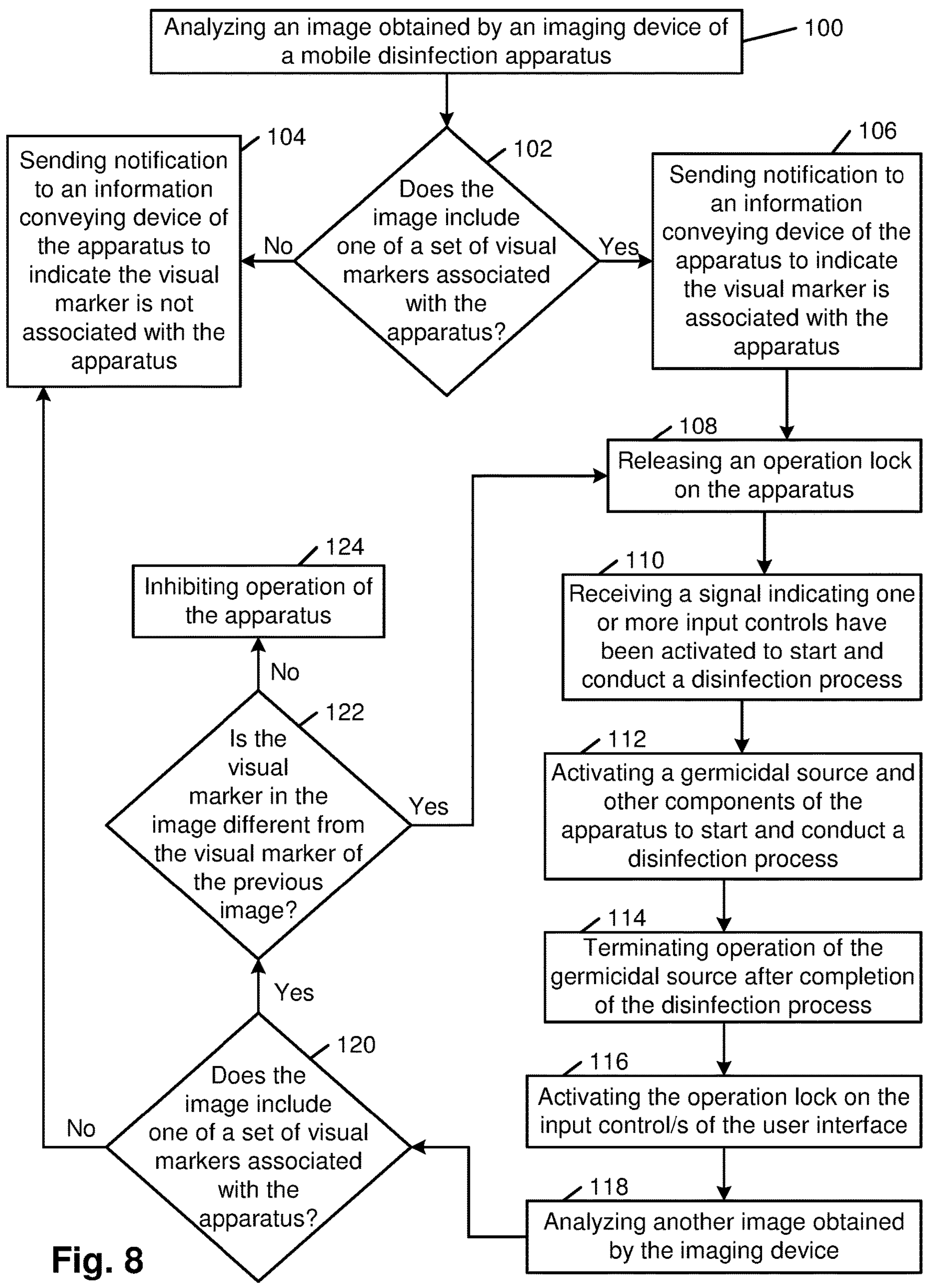

FIG. 8 shows a flowchart including block 100 denoting program instructions for analyzing an image obtained by an imaging device of a mobile disinfection apparatus. Such a process may take many forms as described above, including but not limited to comparing the image to a database of images, comparing the image to one or more previous images taken by the imaging device, analyzing the size, shape, contour, clarity and/or placement of a visually identifiable mark in the image, and/or decoding the image. As shown in block 102 of FIG. 8, the analysis process denoted in block 100 may lend to a determination of whether the image includes one of a set of one or more visual markers associated with the mobile disinfection apparatus. As set forth above, "a visual marker associated with a mobile apparatus", as used herein, refers to a visual marker that is linked with a mobile apparatus having a means for detecting or identifying the visual marker or a classification thereof. In addition or alternatively, "a visual marker associated with a mobile apparatus" may refer to a visual marker having a means for detecting a mobile apparatus that is linked to the visual marker.

As further set forth above, the means of a visual marker or of a mobile apparatus to detect each other and particularly determine whether they are associated with each other may take many forms. Examples of such means may include but are not limited to program instructions for analyzing an image of a visual marker, the imaging device of the mobile apparatus, and/or the visual maker and mobile apparatus respectively having a wireless signal receiver and transceiver or vice versa. As such, although the program instructions described in reference to blocks 100 and 102 of FIG. 8 are specific to analyzing an image of a visual marker, it is noted that other manners of determining whether a detected visual marker is associated with a mobile disinfection apparatus may be used in conjunction with the other processes set forth in FIG. 8.

In some cases, visual marker/s associated with a mobile apparatus may include one or more visually identifiable marks. The visually identifiable mark/s may include but are not limited to characters (numerical, alphabetical and/or alphanumerical), geometric shapes, symbols, pictorial images as well as linear barcodes and matrix barcodes (e.g., QR codes). In cases in which there are multiple visual markers associated with a mobile apparatus, the visual identifiable marks may be the same among all the visual markers or may be different among some or all of the visual markers. In any case, the analysis of an image obtained by an imaging device denoted in block 100 of FIG. 8 may, in some cases, include analyzing the size, shape, contour, clarity and/or placement of one or more visually identifiable marks in the image and the process denoted in block 102 of FIG. 8 may include determining whether the one or more analyzed marks matches one or more visual indicia associated with the mobile disinfection apparatus.

In yet other cases in which one or more visual markers associated with a mobile disinfection apparatus each include data embedded marks, each of the visual markers may include an identifying code embedded therein. In such cases, the analysis of an image obtained by an imaging device denoted in block 100 of FIG. 8 may include decoding the image to obtain its identifying code and the process denoted in block 102 of FIG. 8 may include determining whether the obtained identifying code is an identifying code associated with the mobile disinfection apparatus. In cases in which there are multiple visual markers associated with a mobile apparatus, the identifying codes among all the visual markers may, in some cases, be the same. In other cases, identifying codes among some or all of the visual markers may be different. In particular, it may be advantageous for one or more visual markers to have individualized identifying codes such that the codes may be associated with the respective locations of the visual markers or respective operating parameters at which to operate the mobile disinfection apparatus at each visual marker, such as described in more detail below in reference to FIGS. 9 and 10.

As denoted in block 104 of FIG. 8, a mobile disinfection apparatus may, in some cases, include program instructions for sending notification to an information conveying device communicably coupled to the apparatus to indicate the visual marker is not associated with the mobile disinfection apparatus when the determination at block 102 is negative. Conversely, as denoted in block 106 of FIG. 8, a mobile disinfection apparatus may, in some cases, include program instructions for sending notification to an information conveying device communicably coupled to the apparatus to indicate the visual marker is associated with the apparatus when the determination at block is affirmative. In general, the notification/s may be sent via any one or more visual or audible indicators associated with the mobile disinfection apparatus. In some cases, a mobile disinfection apparatus may not include program instructions for sending a notification to indicate a visual marker is associated with the apparatus and thus, in some cases, block 106 may be omitted from the method outlined in FIG. 8. In such cases, other program instructions of the mobile disinfection apparatus may be activated upon determining an image includes a visual marker associated with the apparatus, such as but not limited to releasing an operation lock on the apparatus as described in more detail below in reference to block 108 of FIG. 8.

To such a regard, the mobile disinfection apparatuses and methods disclosed herein may, in some cases, include program instructions to place an operation lock on a mobile disinfection apparatus. In some cases, the operation lock may be selectively applied to certain operations of the mobile disinfection apparatus, such but not limited to operations to start and conduct a disinfection process and/or operations to activate a germicidal source of the apparatus. In this manner, the entire operation of the apparatus may not be prohibited. For example, it may be advantageous to allow automated movement of a mobile disinfection apparatus and/or operations of the apparatus's imaging system while inhibiting activation of a disinfection cycle by the apparatus. In some embodiments, the operation lock may be placed on input control/s of a user interface of the apparatus. In this manner, selection of the input control/s will not induce the associated operation. In other cases, the operation lock may be placed on circuitry that induces one or more particular actions by the apparatus. In yet other cases, the operation lock may be placed on the central processing unit to inhibit the activation of program instructions to induce one or more particular actions by the apparatus.

In any case, program instructions to place an operation lock on a mobile disinfection apparatus may be activated in response to a variety of scenarios, depending on the application of the disinfection apparatus. For example, the program instructions to place an operation lock on a mobile disinfection apparatus may be activated upon receiving a signal from an input control on a user interface of the apparatus (i.e., a user of the apparatus may instigate the lock on a mobile disinfection apparatus). In other cases, program instructions to place an operation lock on a mobile disinfection apparatus may be automatically activated after completion of each disinfection process conducted by the apparatus, such as upon termination of a germicidal source of the apparatus. In yet other cases, program instructions to place an operation lock on a mobile disinfection apparatus may be automatically activated upon detecting the apparatus has entered a particular area/room, such as but not limited to an operating room, a patient room, an intensive care unit, a burn unit, a clean room, an area/room associated with a pathogen outbreak, or an area/room currently or previously occupied by a person having an infectious disease. In particular, it may be more important to verify and/or accurately position a mobile disinfection apparatus in some areas/rooms of a building versus others prior to activating the apparatus to start and conduct a disinfection process therein and, thus, it may be advantageous for a mobile disinfection apparatus, in some cases, to have program instructions to selectively engage a lock on the apparatus upon entering particular areas/rooms.

In any case, when a mobile disinfection apparatus includes program instructions to place an operation lock on the apparatus, the apparatus includes program instructions for releasing the operation lock. In some cases, the program instructions to release the operation lock may be activated upon receiving a signal from an input control on a user interface of the apparatus (i.e., a user of the apparatus may instigate the release of the operation lock). In other cases, program instructions to release an operation lock on a mobile disinfection apparatus may be automatically activated upon receipt of a signal from another component of the apparatus indicating a specific occurrence or a provision or condition regarding the apparatus has been met. For example, a mobile disinfection apparatus may include program instructions to release an operation lock on a mobile disinfection apparatus upon receipt of signal/s from an imaging device of the apparatus or from a central processing unit of the apparatus after it analyzes (i.e., processes information regarding) an image taken by an imaging device of the apparatus.

As shown in block 108 of FIG. 8, an operation lock on a mobile disinfection apparatus may be released after determining or receiving notification that the apparatus is positioned in relation with a visual marker associated with the apparatus. Such a provision may be advantageous for ensuring the apparatus is positioned in a correct location in an area/room for conducting a disinfection process. That said, although FIG. 8 offers an example compilation of program instructions in which to include a release of an operation lock on a mobile disinfection apparatus, the process is not limited to being used in conjunction with the processes outlined in FIG. 8. For example, an operation lock on a mobile disinfection apparatus may alternatively be released subsequent to determining or receiving notification that a visual marker is within the field of view of an imaging device, such as in response to either of the processes described in reference to blocks 50 and 52 of FIG. 3. In other cases, an operation lock on a mobile disinfection apparatus may be released subsequent to determining or receiving notification that a visual marker in an image is different from a visual marker of a previous image obtained by the apparatus, such as in response to either of blocks 82 and 86 of FIG. 6 or as shown by the line connecting blocks 122 and block 108 in FIG. 8. In yet other cases, an operation lock on a mobile disinfection apparatus may be released subsequent to determining or receiving notification that an amount of variation of the visual marker in the image relative to a target placement is equal to or less than a predetermined threshold or a corrective action has been activated to affect such a variation amount as described in reference to blocks 92, 94 and 98 of FIG. 7. Such a provision may be advantageous for ensuring the apparatus is placed in a suitable position in relation to a visual marker before the apparatus is activated to start and conduct a disinfection process.

Despite the aforementioned discussion, the mobile disinfection apparatuses disclosed herein need not have an operation lock. Thus, in some cases, block 108 may be omitted from FIG. 8. In such cases, other program instructions of the mobile disinfection apparatus may be activated subsequent to determining an image includes a visual marker associated with the apparatus, such as but not limited to activating a germicidal source and other components of the apparatus to start and conduct a disinfection process as described in more detail below in reference to block 112 of FIG. 8. The program instructions denoted in block 112 may be devised to execute any of the processes described above with respect to block 54 in FIG. 3, which are referenced for block 112 but are not reiterated for the sake of brevity. Additional or alternative program instructions which may be activated subsequent to determining an image includes a visual marker associated with an apparatus include but are not limited to determining whether an amount of variation of the visual marker in the image relative to a target placement is equal to or less than a predetermined threshold as described in reference to block 90 of FIG. 7. Yet other program instructions which may be activated subsequent to determining an image includes a visual marker associated with an apparatus include analyzing the visual marker to determine one or more operating parameters of the mobile disinfection apparatus to conduct a disinfection process at such a location as described in reference to block 130 of FIG. 9 or to determine and convey location-specific information as described in more detail below in reference to blocks 150 and 152 of FIG. 10.

In any case, when a mobile disinfection apparatus includes input control/s to start and conduct a disinfection process, the apparatus will include program instructions to receive signal/s indicating the input control/s have been triggered to activate a germicidal source and other components of the disinfection apparatus to start and conduct a disinfection process as denoted in block 110 of FIG. 8. It is noted, however, that a mobile disinfection apparatus may additionally or alternatively include program instructions to activate a germicidal source and other components of the disinfection apparatus to start and conduct a disinfection process upon receipt of signal/s from other components of the apparatus. For example, a mobile disinfection apparatus may include program instructions to activate a germicidal source and other components of the disinfection apparatus to start and conduct a disinfection process upon receipt of signal/s from an imaging device of the apparatus or from a central processing unit of the apparatus after it analyzes (i.e., processes information regarding) an image taken by an imaging device of the apparatus. In some cases, a mobile disinfection apparatus may include program instructions to activate a germicidal source and other components of the disinfection apparatus to start and conduct a disinfection process upon detecting a particular occurrence or determining a provision or condition has been met, such as but not limited to such as in response to any of the processes described above in reference to blocks 50 and 52 of FIG. 3, blocks 82 and 86 of FIG. 6, blocks 92, 94 and 98 of FIG. 7, and block 102, 106 and 122 in FIG. 8.

In any case, a mobile disinfection apparatus may include program instructions to terminate operation of its germicidal source after completion of a disinfection process as denoted in block 114 of FIG. 8. With regard to such a process, reference is made to the description set forth above regarding program instructions for terminating a germicidal source of a mobile disinfection apparatus upon receipt of a signal indicating a disinfection process is complete, particularly that the signal may be from a timer in the apparatus, a germicidal dose sensor communicably coupled to the apparatus, or a user interface of the apparatus. As noted above and denoted in block 116 of FIG. 8, a mobile disinfection apparatus may, in some cases, include program instructions to lock input control/s on a user interface of a mobile disinfection apparatus after completion of a disinfection process conducted by the apparatus. In other cases, however, an operation lock need not be placed on the input control/s of the user interface and, thus, block 116 may be omitted from FIG. 8 in some cases.

As further noted above in reference to block 56 of FIG. 3, a mobile disinfection apparatus may, in some case, be repositioned subsequent to the apparatus completing a disinfection process such that a different visual marker is within a field of view of an imaging device of the apparatus. Furthermore, as described in reference to block 84 of FIG. 6 and denoted in block 118 of FIG. 8, a mobile disinfection apparatus may include program instructions to analyze another image obtained by the imaging device, particularly after the apparatus is repositioned. Such a process may take many forms as described above, including but not limited to comparing the image to a database of images, comparing the image to one or more previous images taken by the imaging device, analyzing the size, shape, contour, clarity and/or placement of a visually identifiable mark in the image, and/or decoding the image. Subsequent to the image analysis, a mobile apparatus may execute program instructions to determine whether the image includes one of a set of visual markers associated with the apparatus as denoted in block 120 in FIG. 8. The program instructions may be devised to execute any of the processes described above with respect to block 102 in FIG. 8, which are referenced for block 120 but are not reiterated for the sake of brevity.

As shown in FIG. 8, when it is determined at block 120 that an image does not include a visual marker associated with the apparatus, the mobile disinfection apparatus may divert to its program instructions denoted in block 104, i.e., to send notification to an information conveying device communicably coupled to the apparatus to indicate the visual marker is not associated with the apparatus. Conversely, when it is determined at block 120 that an image includes a visual marker associated with the apparatus, the mobile disinfection apparatus may divert to program instructions denoted in block 122 to determine whether the visual marker in the image is different from the visual marker of the previous image. In particular, it may be advantageous to determine if the mobile disinfection apparatus has been suitably moved in an area/room for a subsequent disinfection process. The program instructions denoted in block 122 may be devised to execute any of the processes described above with respect to block 82 in FIG. 6, which are referenced for block 122 but are not reiterated for the sake of brevity. Furthermore, it is noted that the order at which the processes conducted in reference to block 120 and 122 may be reversed.

In any of such cases, as shown in FIG. 8, a mobile disinfection apparatus may execute the program instructions denoted in block 124 to inhibit the apparatus from conducting a disinfection process when it is determined at block 122 that an image includes a visual marker that is same as a visual marker of a previously obtained image. Program instructions to inhibit an apparatus from conducting a disinfection process may include any of the processes described above with respect to block 84 in FIG. 6 (which are referenced for block 124 but are not reiterated for the sake of brevity), including but not limited to maintaining an operation lock on input control/s of a user interface of the apparatus to start and conduct a disinfection process. In addition or alternative to executing the program instructions denoted in block 122, a mobile disinfection apparatus may execute the program instructions denoted in blocks 106 and/or 108 of FIG. 8 and/or blocks 90-98 of FIG. 7 when it is determined at block 120 that an image includes a visual marker associated with the apparatus. In yet other embodiments, a mobile disinfection apparatus may execute the program instructions denoted in blocks 106 and/or 108 of FIG. 8 and/or blocks 90-98 of FIG. 7 when it is determined at block 122 that an image includes a visual marker that is different from a visual marker of a previously obtained image. As such, although FIG. 8 illustrates the program instructions denoted in block 108 of FIG. 8 are executed after it is determined in block 122 that an image includes a visual marker that is different from a visual marker of a previously obtained image, the methods and mobile disinfection apparatuses disclosed herein are not necessarily limited to such an order of program instructions to be executed by a mobile disinfection apparatus.

Figures 9, 10:
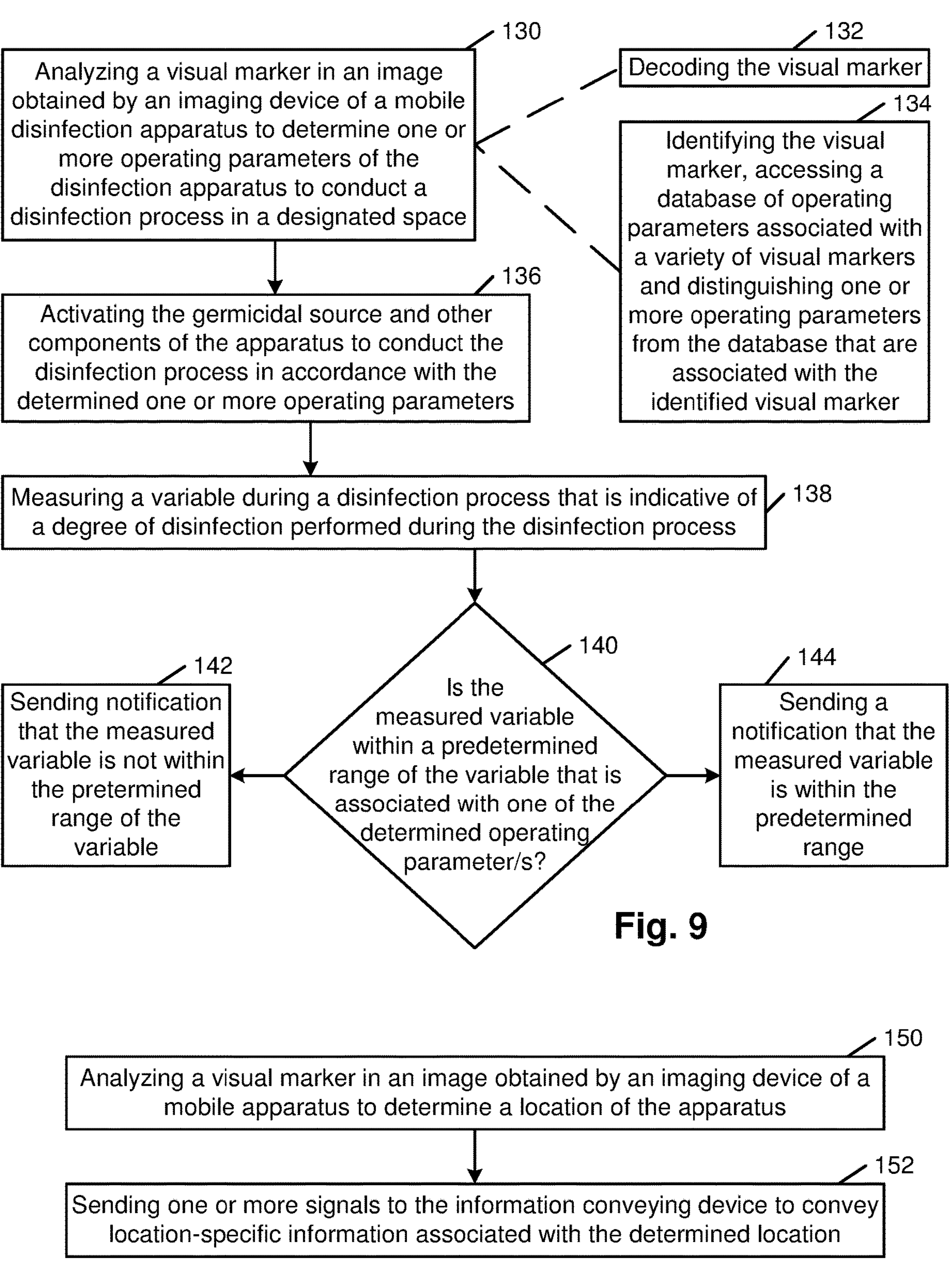

As set forth above, mobile apparatuses and methods are provided herein that utilize visual marker detection systems to affect the operation of a mobile apparatus, particularly to control when and/or what manner the mobile apparatus may be operated. An example set of program instructions directed to such an objective is set forth in FIG. 9. In particular, FIG. 9 shows a flowchart including block 130 denoting program instructions for analyzing a visual marker in an image obtained by an imaging device of a mobile disinfection apparatus to determine one or more operating parameters of the disinfection apparatus to conduct a disinfection process and, in some cases, particularly parameters for generating and/or dispersing a germicidal agent. In addition, FIG. 9 shows the flowchart including block 136 denoting program instructions for activating the germicidal source and other components of the disinfection apparatus to conduct a disinfection process in accordance with the determined one or more operating parameters. In reference to such a process, it is noted that the method outlined in FIG. 9 may include any of process steps and/or provisions for preparing a mobile disinfection apparatus for a disinfection cycle as discussed in reference to FIG. 3 prior to or subsequent to the process referenced in block 136.

As shown in block 132 of FIG. 9, the process of analyzing a visual marker in reference to block 130 may, in some cases, include decoding the visual marker to determine one or more operating parameters of the disinfection apparatus to conduct a disinfection process. In other cases, as shown in block 134 of FIG. 9, the process of analyzing a visual marker in reference to block 130 may include identifying the visual marker in any of the manners described above in reference to block 100 of FIG. 8, accessing a database of operating parameters associated with a variety of visual markers and distinguishing one or more operating parameters from the database that are associated with the identified visual marker.

In any case, the one or more operating parameters referenced in blocks 130 and 136 of FIG. 9 may include any parameter which affects the operation of the mobile disinfection apparatus to conduct a disinfection process. Example operating parameters include but are not limited to run time of a germicidal source of the apparatus, orientation/s of one or more components comprising the apparatus (such as but not limited to the position of a germicidal source in the apparatus and/or the orientation of a reflector in the apparatus if the germicidal source is a lamp), germicidal dosing parameters for the germicidal source and/or power supplied to the germicidal source. In cases in which the germicidal source includes a pulsed germicidal source, such as a flashlamp for example, germicidal dosing parameters for the disinfection source may include pulse duration and/or pulse frequency. Furthermore, in embodiments in which the germicidal source is a flashlamp, power supplied to the flashlamp may be referred to as "pulse intensity" or "intensity of the lamp". In cases in which a mobile disinfection apparatus includes wheels to affect mobility of the disinfection apparatus, a motor to automate movement of the wheels and program instructions to activate the motor during a disinfection process, the operating parameter/s referenced in blocks 130 and 136 of FIG. 9 may, in some cases, additionally or alternatively include a path for the disinfection apparatus to move along during a disinfection process and/or one or more speeds for the disinfection apparatus to move during the disinfection process.

In some cases, the one or more operating parameters determined in block 130 of FIG. 9 may be relayed via a user interface of the mobile disinfection apparatus such that a user of the apparatus may utilize the information to invoke the operating parameter/s for the apparatus. In other cases, the mobile disinfection apparatus may include program instructions to send a command to one or more means within the apparatus for automatically invoking the operating parameter/s determined from a visual marker. For example, in some cases, a mobile disinfection apparatus may include an actuator to move its germicidal source relative to other components of the apparatus, such as but not limited to a base of the apparatus. In some of such cases, the mobile disinfection apparatus may include program instructions to analyze a visual marker to determine a position of the germicidal source for a disinfection process and send a command to the actuator to automatically move the germicidal source to the determined position. Another example of a mobile disinfection apparatus having program instructions to automatically invoke an operating parameter of a disinfection process is a mobile disinfection apparatus having a repositionable reflector and an actuator to move the reflector relative to other components of the apparatus, such as but not limited to a base of the apparatus. In some of such cases, the mobile disinfection apparatus may include program instructions to analyze a visual marker to determine a position of the reflector for a disinfection process and send a command to the actuator to automatically move the reflector to the determined position.

In some cases, the one or more operating parameters determined in block 130 of FIG. 9 may include a schedule of operating parameters for the mobile disinfection apparatus. In such a context, the term "schedule" refers to a series of operating parameter designations to be performed in succession. In some cases, the operating parameter/s determined from a visual marker may include a schedule of the same type of operating parameter. In other cases, the operating parameter/s determined from a visual marker may include a schedule of different types of operating parameters. In any case, a schedule of operating parameters may, in some cases, be for a single disinfection process conducted by the mobile disinfection apparatus. For example, in cases in which a mobile disinfection apparatus has an actuator to move its germicidal source relative to a base of the disinfection apparatus and further has program instructions are for activating the actuator during the disinfection process, the operating parameters determined from a visual marker may include a schedule of positions for the germicidal source to be moved to during the disinfection process. In other cases, however, the schedule of operating parameters may be for multiple disinfection processes conducted by the mobile disinfection apparatus. In either scenario, other examples of a schedule of operating parameters that may be determined from a visual marker may be a schedule of germicidal dosing parameters for the germicidal source, a schedule of orientations of a moveable component of the apparatus, a schedule of power supplied to the germicidal source, a schedule of speeds for the disinfection apparatus to move, a schedule of pulse durations for the germicidal source and/or a schedule of pulse frequencies for the germicidal source.

Another example of a schedule of operating parameters that may be determined from a visual marker may be a schedule of locations within an area/room or among multiple areas/rooms of a building to position the mobile disinfection apparatus. The movement of the mobile disinfection apparatus to the different locations may be manual, may be by user input controls or may be via navigational controls of the apparatus. In some cases, a mobile disinfection apparatus may be configured to respectively conduct distinct disinfection processes at the different locations. In such scenarios, the operating parameter/s determined from a visual marker may, in some cases, additionally include a schedule of run times that coincide with the schedule of locations and/or schedule/s of any one or more other operating parameters noted above. Having a schedule of one or more operating parameters coincide with the schedule of locations may be beneficial if one or more of the locations needs a disinfection process conducted using different parameters to adequately disinfect the location/s versus the other locations (such as but not limited to the disinfection process being longer or shorter than other locations). In other cases, a mobile disinfection apparatus may be configured to conduct a single continuous disinfection process among the schedule of locations (i.e., operation of the germicidal source is not terminated between the different locations). In some of such cases, the operating parameter/s determined from a visual marker may also include a schedule of times to pause the mobile disinfection at each of the schedule of locations and/or schedule/s of any one or more other operating parameters noted above.

In some cases, the process denoted in reference to block 130 of FIG. 9 may include analyzing an image of the visual maker to determine a location of the mobile disinfection apparatus in the area/room in addition to determining one or more operating parameters of the apparatus to conduct a disinfection process. In other cases, the mobile disinfection apparatus may be configured to determine its location in an area/room independent of the visual marker. For example, a mobile disinfection apparatus may include one or more distance sensors to determine its distance from boundary walls of the area/room or intervening objects. Alternatively, a mobile disinfection apparatus may include a global positioning system, an RFID scanner or any wireless reader (e.g., radio frequency, infrared, wi-fi, Bluetooth, satellite, etc.) for determining its location in an area/room. In yet other cases, a mobile disinfection apparatus may not be configured to determine or verify its location in an area/room.

In some of the cases in which a mobile disinfection apparatus is configured to determine or verify its location in an area/room by analyzing a visual marker, the mobile disinfection apparatus may include program instructions to utilize the location information of the apparatus to convey location-specific information to a user interface of the apparatus. An example set of program instructions directed to such an objective is set forth in FIG. 10. In particular, FIG. 10 shows a flowchart including block 150 denoting program instructions for analyzing an image of a visual marker obtained by an imaging device of a mobile apparatus to determine a location of the apparatus within a structure, such as but not limited to a building, cruise ship, submarine, or airplane. In addition, FIG. 10 shows the flowchart having block 152 denoting program instructions for sending one or more signals to an information conveying device of the apparatus to convey location-specific information associated with the determined location. Although the noted program instructions are not necessarily so limited, in some cases the location-specific information may specifically include infection control information, such as but not limited to an isolation status of the determined location or a notice of a pathogen outbreak at the determined location. In some cases, the location-specific information may include instructions for affecting one or more activities by a user of the apparatus. For example, the location-specific information may include instructions to wear one or more infection control items, such as but not limited to gloves, facemasks, respirators, goggles, and/or other infection control apparel.

In some cases, the mobile apparatus referenced for the program instructions denoted in FIG. 10 may be a mobile disinfection apparatus and, in specific cases, may be a robotic disinfection apparatus. However, as noted above, the program instructions set forth in the flowcharts of FIGS. 3-12 are not necessarily limited to mobile disinfection apparatuses and, on the contrary, may be applied to any mobile apparatus. Examples of mobile apparatuses which may include any one or more of the program instructions set forth in the flowcharts of FIGS. 3-12 are mobile medical equipment, such as but not limited to a mobile surgical tray stand, a mobile ventilator, a wheelchair, a gurney, a mobile intravenous stand, a mobile medical utility cart and a mobile vital signs monitor.

Turning to back to FIG. 9, the mobile disinfection apparatuses disclosed herein may, in some cases, include program instructions for determining whether a disinfection process performed by the apparatus is conducted in accordance with one or more operating parameters determined for the apparatus from an analysis of a visual marker that the apparatus is positioned in relation to. In particular, FIG. 9 shows block 138 denoting program instructions for measuring a variable during a disinfection process that is indicative of a degree of disinfection performed during the disinfection process. Examples of the measured variable may include but are not limited to a duration of the disinfection process, power supplied to the apparatus, or a dose (i.e., a cumulative amount or dispersal rate) of a germicide generated and/or projected from the mobile disinfection apparatus during the disinfection process. Another example of a measured variable may be but is not limited to pulse count for cases in which the mobile disinfection apparatus includes a pulsed germicidal source, such as a flashlamp. Yet other examples of measured variables are positions of components used in conjunction with the apparatus, such as but not limited to one or more reflectors and/or lenses (attached or detached from the apparatus) for cases in which the mobile disinfection apparatus includes a germicidal lamp.

As further shown in block 140 of FIG. 9, a mobile disinfection apparatus may include program instructions for comparing the measured variable to a preset value of the variable or a preset range of the variable subsequent to the disinfection apparatus completing the disinfection process. As noted in block 140, the preset value of the variable or the preset range of the variable is associated with one or more operating parameters determined in reference to block 130. It is noted that comparing the measured variable to a preset range of the variable may aid in accommodating slight variations in the performance of the mobile disinfection apparatus versus its expectation, but in cases in which precision is desired in determining whether a disinfection process is conducted in accordance with one or more operating parameters determined for the apparatus, the comparing process may include comparing the measured variable to a preset single value of the variable.

In any case, the variable measured in reference to block 138 and the one or more operating parameters determined in reference to block 130 may, in some cases, be the same factors of the disinfection process. For example, in some cases, an operating parameter determined in reference to block 130 and the variable measured in reference to block 138 may be run times of the mobile disinfection apparatus. In other cases, an operating parameter determined in reference to block 130 and the variable measured in reference to block 138 may be germicidal doses generated and/or projected from the mobile disinfection apparatus. In yet other cases, an operating parameter determined in reference to block 130 and the variable measured in reference to block 138 may be pulse counts of a pulsed germicidal source of the mobile disinfection apparatus.

For example, in cases in which run time is the determined operating parameter and the measured variable, the comparison process of block 140 may include comparing the measured run time of the disinfection apparatus to a run time determined in reference to block 130 or to a range of durations comprising the run time determined in reference to block 130. For instance, if a run time of a disinfection process to be performed by a mobile disinfection apparatus is determined to be 5 minutes and 0 seconds in reference to block 130 and the run time of the actual disinfection process measured in reference to block 138 is 5 minutes and 7 seconds, the comparison process conducted in reference to block 140 may involve comparing the measured run time of 5 minutes and 7 seconds to the determined run time of 5 minutes and 0 seconds. Alternatively, the comparison process conducted in reference to block 140 may involve comparing the measured run time of 5 minutes and 7 seconds to a range of run times between 4 minutes and 45 seconds and 5 minutes and 15 seconds, which is inclusive to the determined run time of 5 minutes and 0 seconds.

Alternatively, the variable measured in reference to block 138 and the one or more operating parameters determined in reference to block 130 may be different factors of the disinfection process. For example, in some cases, an operating parameter determined in reference to block 130 may be run time of the mobile disinfection apparatus and the variable measured in reference to block 138 may be pulse count of a pulsed germicidal source of the mobile disinfection apparatus. In such cases, the comparison process of block 140 may include comparing the measured pulse count to a specified pulse count or a range of pulse counts associated with the run time determined from analyzing the image of the visual marker in reference to block 130. More specifically, the comparison process of block 140 may include comparing the measured pulse count to a pulse count that is expected to approximately equate to the run time determined from analyzing the image of the visual marker in reference to block 130 or to a predetermined range of pulse counts which encompasses that pulse count. For instance, if a run time of a disinfection process is set to be 5 minutes and a germicidal source of the mobile disinfection source is set to pulse at 1.5 Hz during a disinfection process, the number of pulses expected at the end of such a run time is 450 pulses. In such cases, the comparison process of block 140 may include comparing the measured pulse count to 450 pulses or to a predetermined range of pulses, such as between 425 pulses and 475 pulses.

Other combinations of factors of a disinfection process (i.e., other than the example noted above) may also or alternatively be determined, measured, and compared in reference to blocks 130, 138 and 140. In particular, for a given disinfection process, run time, germicidal dose, power supplied, component position, and pulse count (if applicable) may be interrelated and, thus, comparing measured values and assigned values among any combination of such factors for a disinfection process may be used to determine whether a disinfection process performed by the apparatus is conducted in accordance with one or more operating parameters predetermined for the apparatus. In any case, as shown in block 142 of FIG. 9, a mobile disinfection apparatus may include program instructions for sending a notification upon determining the measured variable does not meet the preset value of the variable or is not within the preset range of the variable. In some cases, a mobile disinfection apparatus may additionally include program instructions for sending a notification upon determining the measured variable meets the preset value of the variable or is within the preset range of the variable as denoted in block 144 of FIG. 9. Alternatively, a mobile disinfection apparatus may not include program instructions for the notification referenced in block 144. In some cases, either or both of the notifications referenced in blocks 142 and 144 may be sent to an information conveying device of the mobile disinfection apparatus. In addition or alternatively, either or both of the notifications referenced in blocks 142 and 144 may be sent to a database or memory which is communicably coupled to the mobile disinfection apparatus for recording the results.

Figures 11, 12:
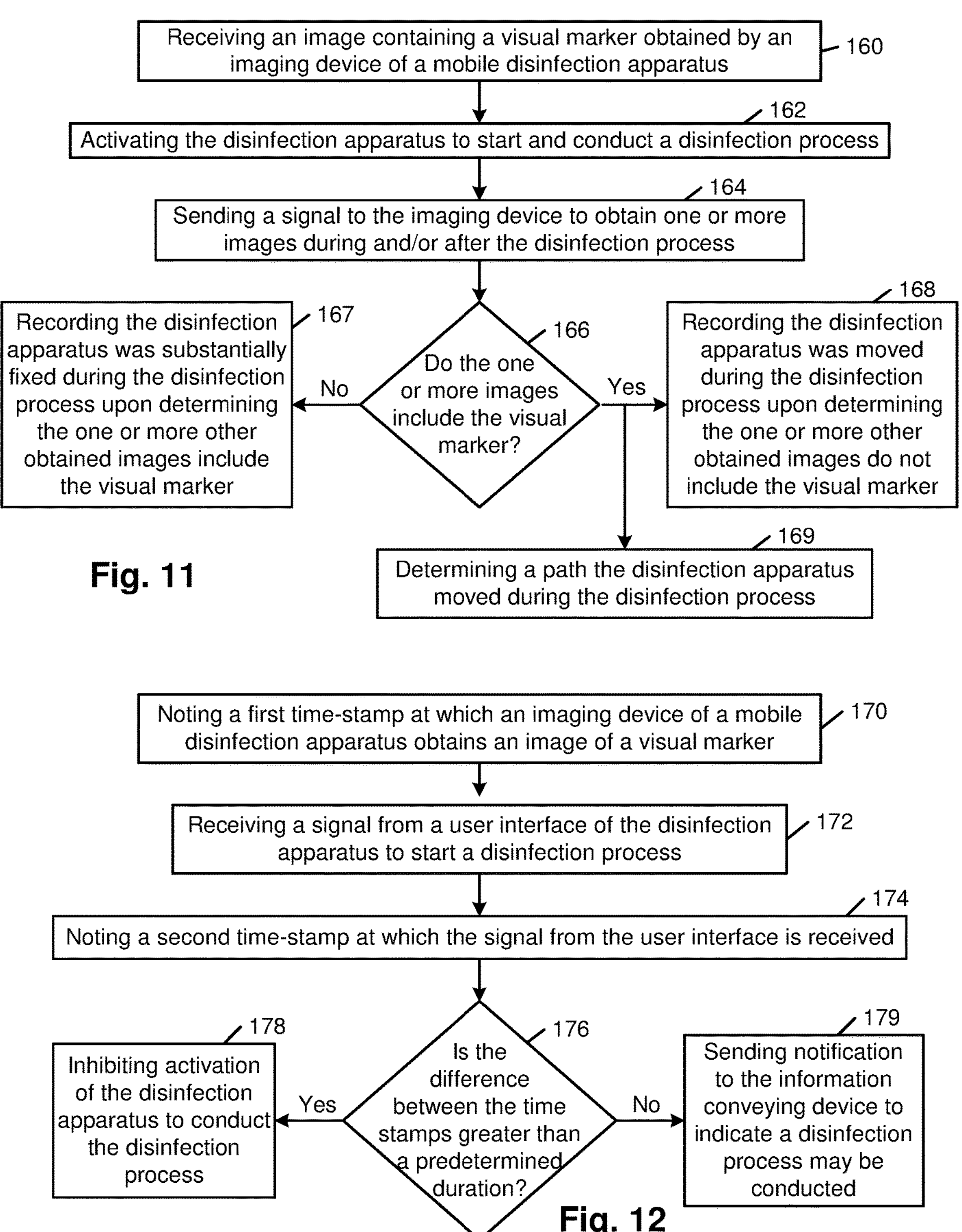

In some cases, a mobile disinfection apparatus may include program instructions to determine whether the apparatus moves prior to or during a disinfection process. An example set of program instructions directed to such an objective is set forth in FIG. 11. In particular, FIG. 11 shows a flowchart including block 160 denoting program instructions for receiving an image containing a visual marker that is obtained by an imaging device of a mobile disinfection apparatus. In some cases, a mobile disinfection apparatus having such program instructions may further include program instructions for analyzing the image as described above in reference to block 80 of FIG. 6, block 100 of FIG. 8, block 130 of FIG. 9, and block 150 of FIG. 10, which are not reiterated for the sake of brevity but are referenced as if fully considered for block 160 of FIG. 11. In other cases, however, a mobile disinfection apparatus need not include image analysis program instructions for the process referenced in block 160, particularly if mobile disinfection apparatus does not include program instructions to conduct the sequence of process steps denoted in any of FIGS. 6-10. In particular, a mobile disinfection apparatus may, in some cases, receive an image of a visual marker in reference to block 160 of FIG. 11 simply for comparison of images obtained during and/or after a disinfection process performed by the mobile disinfection apparatus and, thus, the analysis of the image prior to block 166 may not be necessary.

In any case, the flowchart illustrated in FIG. 11 includes block 162 denoting program instructions for activating the mobile disinfection apparatus to start and conduct a disinfection process subsequent to receiving the image referenced in block 160. The process denoted in block 162 may generally include any of the processes described in reference to block 54 of FIG. 3, block 112 of FIG. 8 and block 136 of FIG. 9, which are not reiterated for the sake of brevity but are referenced as if fully considered for block 162 of FIG. 11. In some cases, one or more process steps and/or provisions may be conducted prior or subsequent to the mobile disinfection apparatus being activated to start and conduct a disinfection process. Examples of tasks to be performed before a germicidal source is activated are shown in blocks 64, 66 and 68 of FIG. 3 as well as block 76 of FIG. 5 but it is noted that additional and/or alternative tasks may be performed to prepare an area/room for a disinfection process. In any case, as shown in block 164 of FIG. 11, a mobile disinfection apparatus may include program instructions for sending one or more signals to its imaging device to obtain one or more images during and/or after the disinfection process. More specifically, a mobile disinfection apparatus may include program instructions for sending one or more signals to its imaging device to obtain one or more images subsequent to its germicidal source being initially activated and sometime before and/or after operation of the germicidal source is terminated. The timing at which to obtain the images may be preset and, in some cases, may be periodic.

In some cases, the program instructions associated with the process denoted in block 164 may be specific to sending the signal/s a predetermined amount of time after operation of the germicidal source is terminated. In some such cases, it may be advantageous to have the predetermined amount of time to be a relatively short increment of time, particularly a shorter amount of time than the apparatus is expected be moved to a different location. Example of time increments may be but are not limited to less than approximately 3 minutes and, in some cases, less than approximately 1 minute. In particular, having the imaging device prompted to obtain one or more images a relatively short increment of time after operation of the germicidal source is terminated may be advantageous to improve the likelihood the additional image/s reflect the position of the apparatus at the end of the disinfection process most recently conducted by the apparatus. On the contrary, if the imaging device is prompted to obtain one or more images a relatively long amount of time after operation of the germicidal source is terminated, the additional image/s may not reflect the position of the apparatus in relation to the most previous disinfection process conducted by the apparatus. For instance, in some cases, a mobile disinfection apparatus may be programmed or scheduled to be moved after a present amount of time to a different location for a different disinfection process after a disinfection process at a first location is complete. In such cases, image/s obtained after the preset amount of time will not correlate to the disinfection process most recently conducted.

As noted in block 166 of FIG. 11, a mobile disinfection apparatus may include program instructions for determining whether the one or more images obtained during and/or after the disinfection process include the visual marker of the image received in reference to block 160. In some cases, such a process may involve comparing the one or more images to the image received in reference to block 160. In other cases, such a process may involve analyzing the one or more image/s to determine whether they include a visual marker and if they do, identifying the visual marker and comparing to the identification of the visual marker determined from the image received in reference to block 160. In such cases, the mobile disinfection apparatus includes program instructions to analyze the image received in reference to block 160 to identify the visual marker therein. In any case, as shown in block 167 of FIG. 11, the mobile disinfection apparatus may include program instructions to record the apparatus as being substantially fixed during the disinfection process upon determining the one or more images obtained during and/or after the disinfection process include the visual marker of the image received in reference to block 160. In cases in which a mobile disinfection apparatus includes program instructions to determine a location of the apparatus from analyzing the image received in reference to block 160, the program instructions denoted in block 167 of FIG. 11 may record the apparatus as being substantially fixed to such a location during the disinfection process.

In any case, as denoted in block 168 of FIG. 11, a mobile disinfection apparatus may include program instructions to record that the apparatus was moved during the disinfection process upon determining the one or more images obtained during and/or after the disinfection process do not include the visual marker of the image received in reference to block 160. In addition or alternatively, as denoted in block 169 of FIG. 11, a mobile disinfection apparatus may include program instructions to determine, and in some cases record, a path the disinfection apparatus moved during the disinfection process upon determining the one or more images obtained during and/or after the disinfection process do not include the visual marker of the image received in reference to block 160. In such cases, visual markers in the image/s obtained during and/or after the disinfection process may be used in conjunction with the image received in reference to block 160 to determine the path the disinfection apparatus moved. In some cases, the process denoted in reference to block 169 may involve listing the identifications and/or locations of the visual markers in chronological order in reference to the timing in which their respective images were obtained. In other cases, the process denoted in reference to block 169 may involve mapping the locations of the visual markers in a rendition of the area/room in which the disinfection process was performed and linking the visual markers by arrowed lines in the order in which their respective images were obtained.

In some cases, the mobile disinfection apparatuses disclosed herein may include program instructions to affect the activation of the apparatus to conduct a disinfection process based on the timing at which a signal is received from a user interface of the apparatus to start and conduct a disinfection process relative to the timing at which an imaging device of the apparatus obtains an image of a visual marker. Such a process may be beneficial for ensuring that a disinfection cycle is conducted at a location associated with a particular visual marker. An example set of program instructions directed to such an objective is set forth in FIG. 12. In particular, FIG. 12 shows a flowchart including block 170 denoting program instructions for noting a first timestamp at which the imaging device of a mobile disinfection apparatus obtains an image of a visual marker. In addition, the flowchart illustrated in FIG. 12 includes blocks 172 and 174 respectively denoting program instructions for receiving a signal from a user interface of the disinfection apparatus to start and conduct a disinfection process and noting a second timestamp at which the signal from the user interface is received.

As shown in block 176 of FIG. 12, a mobile disinfection apparatus may include program instructions to determine whether the difference between the first and second timestamps is greater than a predetermined duration. Further to such and as denoted in block 178 of FIG. 12, the mobile disinfection apparatus includes program instructions to inhibit activation of the disinfection apparatus (i.e., the germicidal source and other components of the apparatus) to conduct the disinfection process if the difference in the first and second time stamps is greater than the predetermined duration. In some cases, as denoted in block 179 of FIG. 12, a mobile disinfection apparatus may include program instructions to send notification to an information conveying device of the apparatus if the difference in the first and second time stamps is less than or equal to the predetermined duration. However, in other cases, a mobile disinfection apparatus may be void of the program instructions denoted in block 179. In any case, it is noted that one skilled in the art would be apprised that the process denoted in block 176 of determining whether the difference is greater than a predetermined duration could be altered to determine whether the dimensional variation is less than a predetermined duration and the execution of the particular actions based thereon may be reversed from the depiction in FIG. 12. Furthermore, it is noted that one skilled in the art would be apprised that the provision of 'or equal to' could be included in either scenario for block 176.

In any case, a mobile disinfection apparatus may include program instructions to record any of the information discussed above in reference to FIGS. 3-12. In general, recording any of such information may be advantageous for providing documentation regarding the placement and the relative operation of the mobile disinfection apparatus. More specifically, the information may be recorded in a database or memory which is communicably coupled to the mobile disinfection apparatus such that it may be recalled at a later time to provide the noted documentation, such as for record keeping purposes and/or for compliance with protocols that define the one or more locations in an area/room at which the device is to be operated for one or more disinfection processes. For example, in some cases, a mobile disinfection apparatus may include program instructions to record a location of the apparatus when a visual marker is in the field of view of an imaging device of the apparatus and/or whether the apparatus has been suitably positioned relative to the visual marker and/or the apparatus has been placed in the vicinity with a visual marker associated with the apparatus. In addition or alternatively, a mobile disinfection apparatus may include program instructions to record the start and stop times of a disinfection process conducted by the apparatus and/or whether a disinfection process is inhibited or terminated prior its set run time.

Moreover, a mobile disinfection apparatus may additionally or alternatively include program instructions to record whether a particular tasks and/or safety precautions are conducted prior to the start of a disinfection process. In some cases, a mobile disinfection apparatus may additionally or alternatively include program instructions to record whether the apparatus moves during a disinfection process conducted by the apparatus or in-between disinfection processes. In addition or alternatively, a mobile disinfection apparatus may include program instructions to record the operating parameters of a disinfection process conducted by the apparatus, specifically the operating parameters set for the apparatus and/or the actual operating parameters. Furthermore, a mobile disinfection apparatus may include program instructions to record measurements taken during disinfection process, such as but not limited to germicidal dosing measurements. Moreover, a mobile disinfection apparatus may additionally or alternatively include program instructions to record what or if any location-specific information was sent to an information conveying device of the apparatus.

It will be appreciated to those skilled in the art having the benefit of this disclosure that this invention is believed to provide mobile apparatuses having visual marker detection systems and methods of their use. Further modifications and alternative embodiments of various aspects of the invention will be apparent to those skilled in the art in view of this description. For example, although the description of the methods and program instructions provided herein are emphasized for use with mobile disinfection apparatuses, the methods and program instructions may be applied to any mobile apparatus and, particularly mobile apparatuses whose operations affect or are affected by the ambient in which they are arranged configured and/or by which the efficacy of its operation is affected by its location in an area/room. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. The term "approximately" as used herein refers to variations of up to +/−5% of the stated number.

What is claimed is:

1. A disinfection apparatus, comprising:
a germicidal source;
an imaging device; and
a controller having a processor and program instructions executable by the processor for:
decoding an image of a visual marker obtained by the imaging device to determine:
a position of the disinfection apparatus in a designated space; and
one or more operating parameters of the disinfection apparatus to conduct a disinfection process in the designated space; and
activating the germicidal source and other components of the disinfection apparatus to conduct the disinfection process in accordance with the determined one or more operating parameters, wherein prior to activating the germicidal source and other components of the disinfection apparatus the program instructions are further for:
noting a first time-stamp at which the imaging device obtains the image of the visual marker;
receiving a signal from a user interface of the disinfection apparatus to start the disinfection process;
noting a second time-stamp at which the signal from the user interface is received; and
inhibiting the activation of the germicidal source and other components of the disinfection apparatus to conduct the disinfection process if the difference between the first and second time-stamps is greater than a predetermined duration.

2. The disinfection apparatus of claim 1, wherein the program instructions are further for:
measuring a variable during a disinfection process that is indicative of a degree of disinfection performed during the disinfection process;
subsequent to the disinfection apparatus completing the disinfection process, comparing the measured variable to a predetermined range of the variable that is associated with one of the determined one or more operating parameters; and
issuing a notification upon determining the measured variable is not within the predetermined range.

3. The disinfection apparatus of claim 2, wherein the variable and the one determined operating parameter are different factors of the disinfection process.

4. The disinfection apparatus of claim 2, wherein the variable and the one determined operating parameter are selected from the group consisting of duration, germicidal dose, and pulse count.

5. The disinfection apparatus of claim 1, further comprising an actuator to move the germicidal source relative to a base of the disinfection apparatus, wherein the program instructions are further for activating the actuator during the disinfection process, and wherein the determined one or more operating parameters comprise a schedule of positions of the germicidal source during the disinfection process.

6. The disinfection apparatus of claim 1, further comprising wheels to affect mobility of the disinfection apparatus and an actuator to automate movement of the wheels, wherein the program instructions are further for activating the actuator during the disinfection process, and wherein the determined one or more operating parameters comprise a path for the disinfection apparatus to move along during the disinfection process and/or one or more speeds for the disinfection apparatus to move during the disinfection process.

7. The disinfection apparatus of claim 1, further comprising a device for conveying information to a user of the disinfection apparatus, wherein the program instructions are further for:
terminating operation of the germicidal source after completion of the disinfection process; and
subsequently sending notification to the information conveying device for a user to move the disinfection apparatus such that a different visual marker disposed in the designated space is within a field of view of the imaging device.

8. The disinfection apparatus of claim 7, wherein the program instructions are further for:
analyzing a different image obtained by the imaging device, wherein the different image is obtained by the imaging device subsequent to the notification being sent to the information conveying device; and
inhibiting activation of the germicidal source and other components of the disinfection apparatus to conduct another disinfection process if the different image includes the first visual marker.

9. The disinfection apparatus of claim 1, wherein the program instructions for activating the germicidal source and other components of the disinfection apparatus comprise program instructions for:
activating an occupancy sensor of the disinfection apparatus; and
subsequently activating the germicidal source to disperse a disinfectant upon the occupancy sensor not detecting occupancy in the designated space for a predetermined amount of time.

10. The disinfection apparatus of claim 1, wherein the one or more operating parameters comprise run time of a germicidal source of the disinfection apparatus, orientation/s of one or more components comprising the disinfection apparatus, germicidal dosing parameters for the germicidal source, and/or power supplied to the germicidal source.

11. The disinfection apparatus of claim 1, wherein the one or more operating parameters comprise a schedule of locations within the designated space to conduct the disinfection process.

12. A disinfection apparatus, comprising:
a germicidal source;
an imaging device;
a device for conveying information to a user of the disinfection apparatus; and
a controller having a processor and program instructions executable by the processor for:
analyzing a first image obtained by the imaging device to determine whether the first image comprises one of a set of designated visual markers associated with the disinfection apparatus;
determining a first amount of dimensional variation between a placement of a visual marker in the first image and a target placement of the visual marker in the first image subsequent to determining the first image comprises one of the set of designated visual markers;
comparing the first amount of dimensional variation to a predetermined threshold of variation; and releasing an operation on the disinfection apparatus subsequent to determining the first amount of dimensional variation is equal to or less than the predetermined threshold.

13. The disinfection apparatus of claim 12, wherein the program instructions are further for determining a corrective action for moving the disinfection apparatus subsequent to determining the first amount of dimensional variation is greater than the predetermined threshold, wherein the corrective action comprises instructions to move the disinfection apparatus such that a second amount of dimensional variation between a placement of the visual marker in a second image subsequently obtained by the imaging device and a target placement of the visual marker in the second image is equal to or less than the predetermined threshold.

14. The disinfection apparatus of claim 13, further comprising wheels and a motor to automate movement of the wheels, wherein the program instructions are further for actuating the motor in accordance with the instructions of the corrective action.

15. The disinfection apparatus of claim 12, wherein the program instructions are further for:

sending a first notification to the information conveying device to indicate the disinfection apparatus has been properly positioned relative to the visual marker subsequent to determining the first amount of dimensional variation is equal to or less than the predetermined threshold;

sending a second notification to the information conveying device to indicate the disinfection apparatus has not been properly positioned relative to the visual marker subsequent to determining the first amount of dimensional variation is greater than the predetermined threshold.

16. A disinfection apparatus, comprising:

a germicidal source;

an imaging device;

a visual display; and a controller having a processor and program instructions executable by the processor for:

displaying on the visual display what the imaging device is viewing in real-time;

analyzing an image obtained by the imaging device to determine whether the image comprises one of a set of designated visual markers associated with the disinfection apparatus; and releasing an operation lock on the disinfection apparatus subsequent to determining the image comprises one of the set of designated visual markers.

17. The disinfection apparatus of claim 16, wherein program instructions are further for decoding a designated visual marker in the image subsequent to determining the image comprises one of the set of designated visual markers to determine:

a position of the disinfection apparatus in a designated space; or one or more operating parameters of the disinfection apparatus to conduct a disinfection process in the designated space.

18. The disinfection apparatus of claim 16, further comprising a sensor for detecting movement of the disinfection apparatus, wherein the program instructions are further for:

monitoring motion of the disinfection apparatus; and subsequent to detecting the disinfection apparatus coming to a stop after moving, sending a signal to the imaging device to obtain an image.

19. The disinfection apparatus of claim 16, wherein the program instructions are further for:

activating the germicidal source and other components of the disinfection apparatus to start and conduct a disinfection process subsequent to releasing the operation lock;

terminating operation of the germicidal source after completion of the disinfection process;

activating the operation lock on the disinfection apparatus subsequent to terminating operation of the germicidal source;

analyzing a different image obtained by the imaging device subsequent to terminating the operation of the germicidal source, wherein the step of analyzing the different image comprises:

determining whether the different image comprises one of the set of designated visual markers associated with the disinfection apparatus; and subsequent to determining the different image comprises one of the set of designated visual markers, determining whether a visual marker in the different image is different than the visual marker in the first image; and releasing the operation lock on the disinfection apparatus subsequent to determining the different image comprises one of the set of designated visual markers and is different from the first visual marker.

* * * * *